(12) United States Patent
Fukuma et al.

(10) Patent No.: US 9,164,110 B2
(45) Date of Patent: Oct. 20, 2015

(54) SAMPLE PROCESSING APPARATUS AND METHOD FOR CONTROLLING A SAMPLE PROCESSING APPARATUS USING A COMPUTER

(71) Applicant: Sysmex Corporation, Kobe-shi (JP)

(72) Inventors: Daigo Fukuma, Kobe (JP); Tetsuya Kaneko, Kobe (JP); Osamu Hirota, Kobe (JP)

(73) Assignee: SYSMEX CORPORATION, Hyogo (JP)

( * ) Notice: Subject to any disclaimer, the term of this patent is extended or adjusted under 35 U.S.C. 154(b) by 453 days.

(21) Appl. No.: 13/722,041

(22) Filed: Dec. 20, 2012

(65) Prior Publication Data

US 2013/0160533 A1    Jun. 27, 2013

(30) Foreign Application Priority Data

Dec. 22, 2011  (JP) ................................. 2011-281604

(51) Int. Cl.
| | | |
|---|---|---|
| G01N 33/00 | (2006.01) | |
| G01N 21/00 | (2006.01) | |
| G01N 35/00 | (2006.01) | |
| G01N 35/02 | (2006.01) | |
| G01N 35/10 | (2006.01) | |
| G01N 33/48 | (2006.01) | |

(52) U.S. Cl.
CPC .......... *G01N 35/00* (2013.01); *G01N 35/00584* (2013.01); *G01N 35/00732* (2013.01); *G01N 35/026* (2013.01); *G01N 35/1004* (2013.01)

(58) Field of Classification Search
CPC .............. G01N 35/026; G01N 35/025; G01N 35/1004; G01N 35/00732; G01N 35/02
USPC ........................................ 422/64, 67, 68.1, 73
See application file for complete search history.

(56) References Cited

U.S. PATENT DOCUMENTS

| | | | | |
|---|---|---|---|---|
| 2001/0039053 | A1* | 11/2001 | Liseo et al. ..................... | 436/43 |
| 2002/0013918 | A1* | 1/2002 | Swoboda et al. ................ | 714/30 |
| 2005/0281707 | A1* | 12/2005 | Nakaya et al. ................... | 422/63 |
| 2006/0165562 | A1* | 7/2006 | Matsubara et al. ........... | 422/100 |
| 2007/0279679 | A1* | 12/2007 | Tanimoto ..................... | 358/1.15 |
| 2008/0063570 | A1* | 3/2008 | Fujino et al. .................... | 422/99 |
| 2010/0108101 | A1* | 5/2010 | Shibata et al. ............. | 134/22.11 |
| 2011/0262303 | A1* | 10/2011 | Burkhardt et al. .............. | 422/64 |

FOREIGN PATENT DOCUMENTS

JP        2003-254980 A        9/2003

\* cited by examiner

*Primary Examiner* — Jill Warden
*Assistant Examiner* — Brittany Fisher
(74) *Attorney, Agent, or Firm* — Brinks Gilson & Lione

(57) ABSTRACT

A sample processing apparatus is disclosed. The apparatus comprises a sample processing section configured to perform a process on a sample; and a controller configured to execute an order defining a process to be performed on a sample and to cause the sample processing section to perform the process on the sample according to the order. When the controller receives an instruction to perform a shutdown operation, the controller performs the following operations comprising: prohibiting the execution of the shutdown operation if an unexecuted order remains; and causing the sample processing section to perform the shutdown operation if there is no unexecuted order.

27 Claims, 18 Drawing Sheets

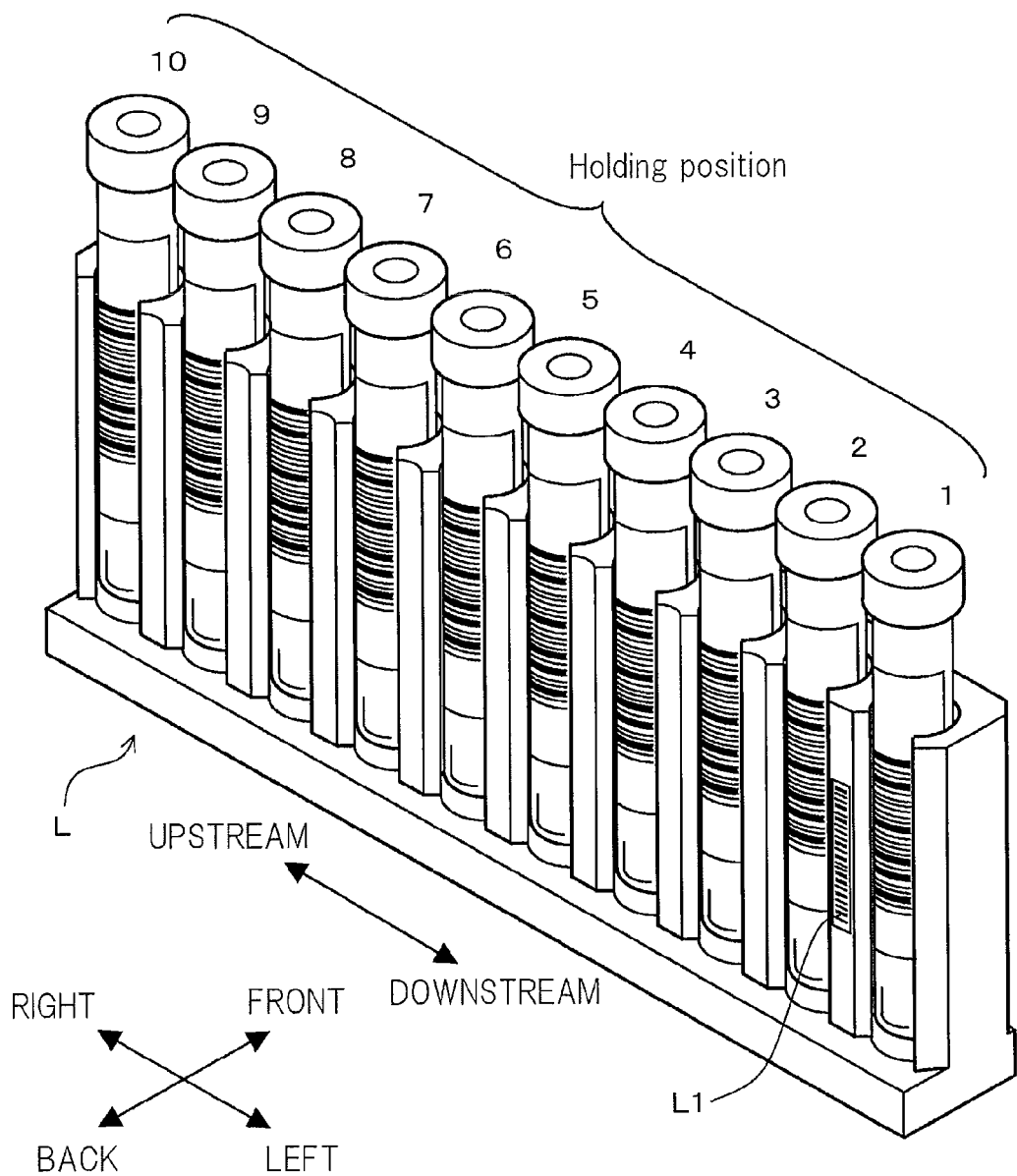

FIG.2D
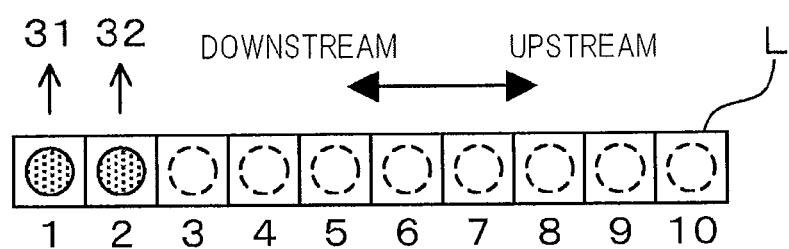
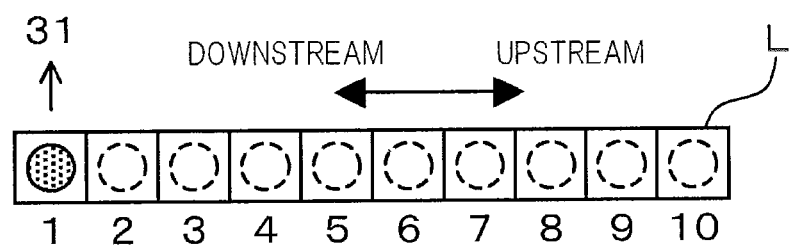
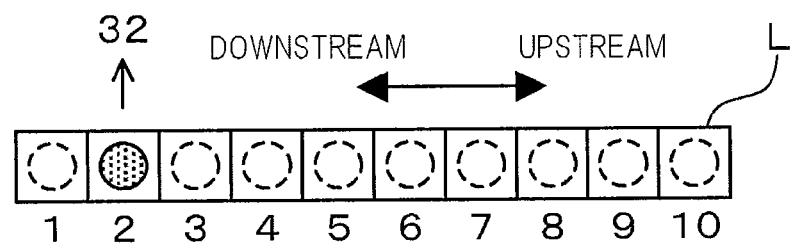

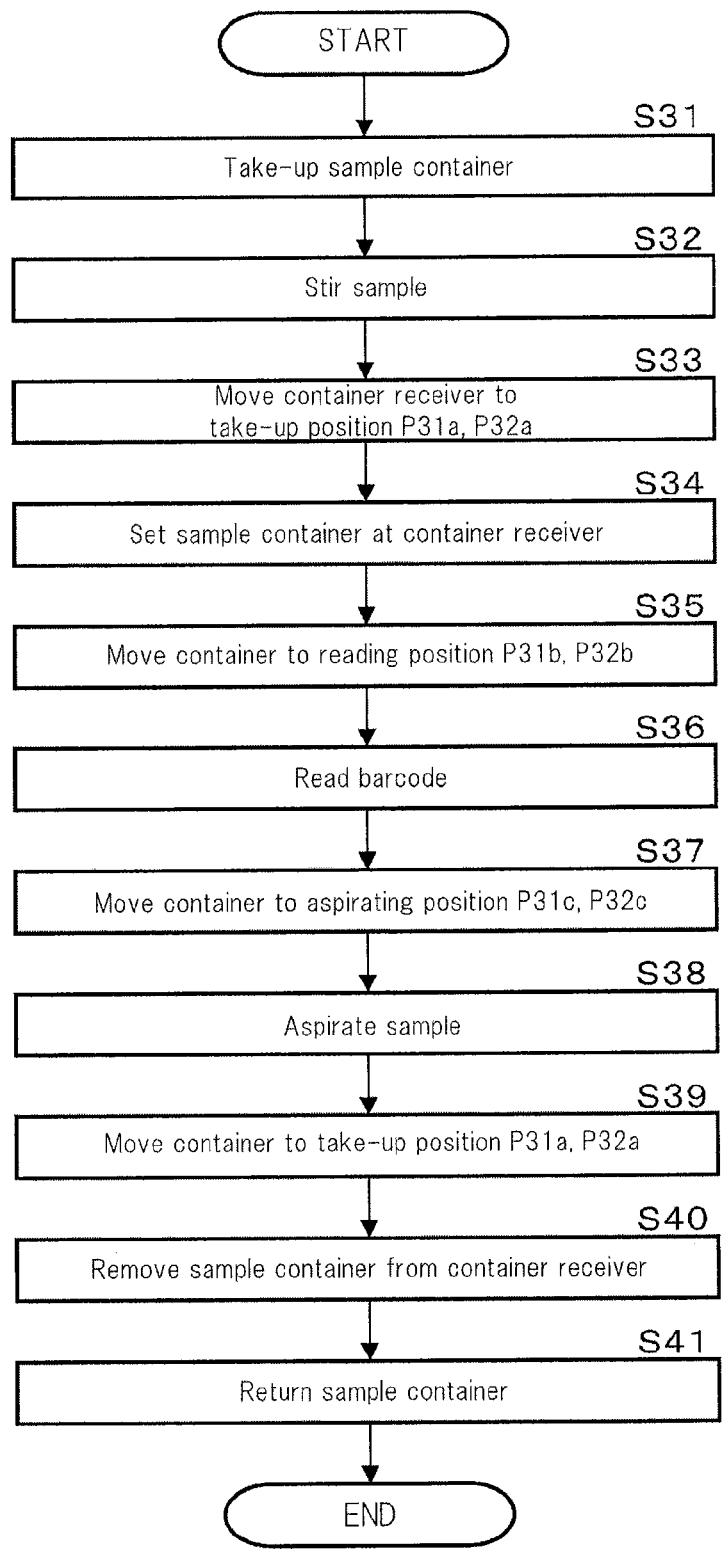
FIG.4A  Sample container take-up operation

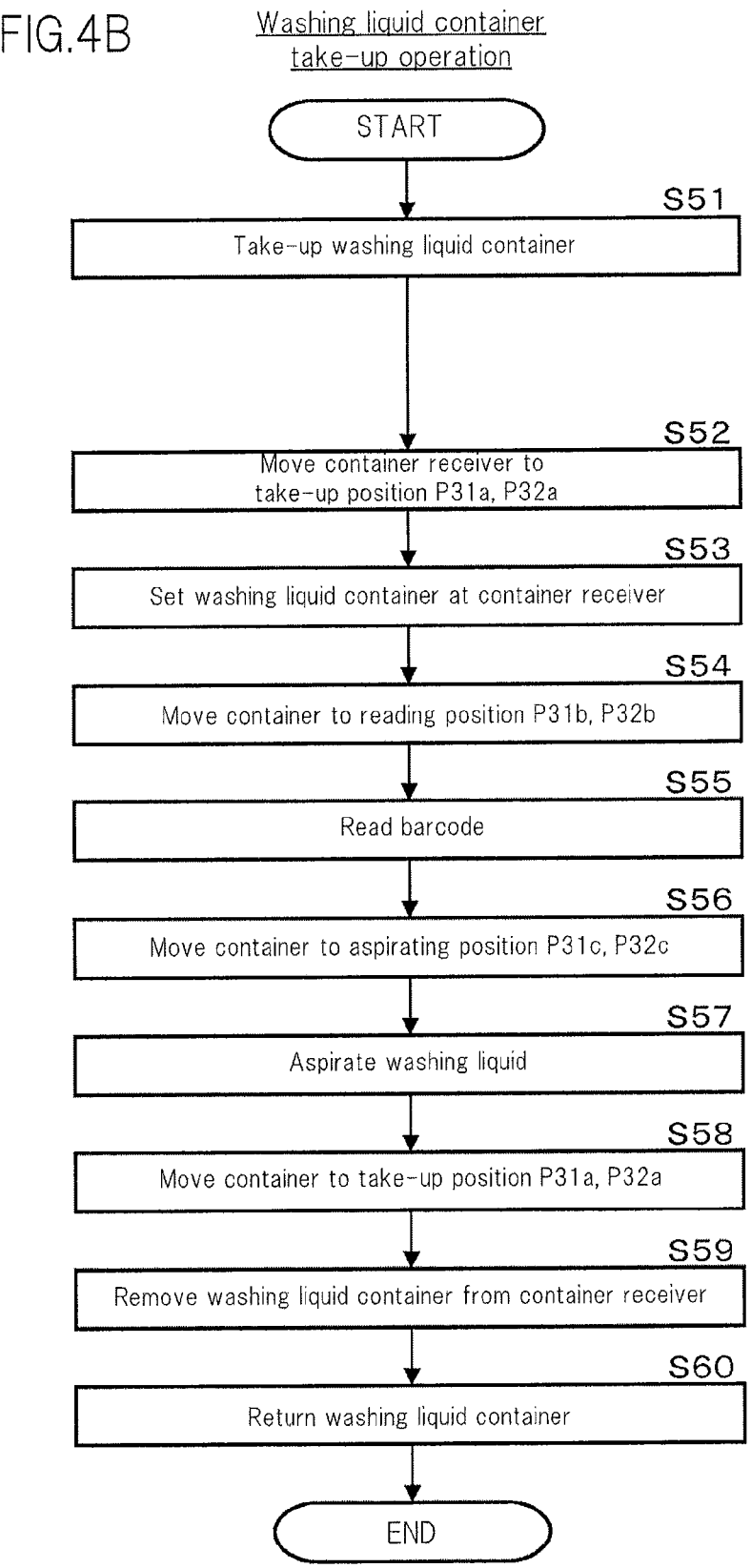

FIG.8

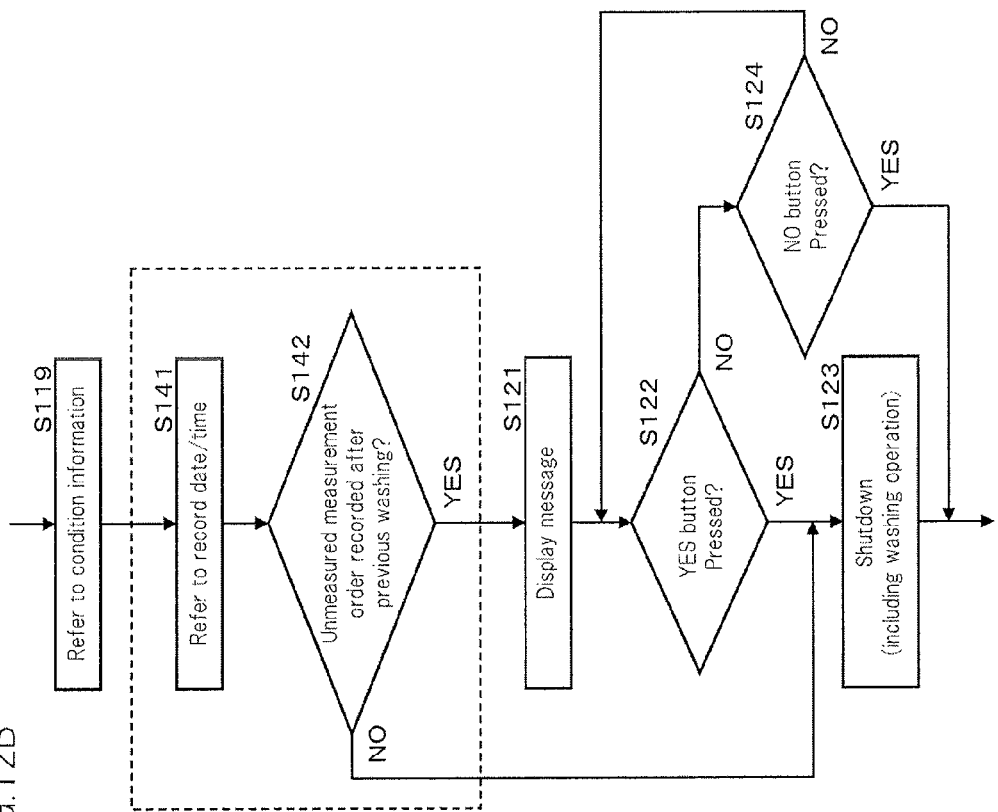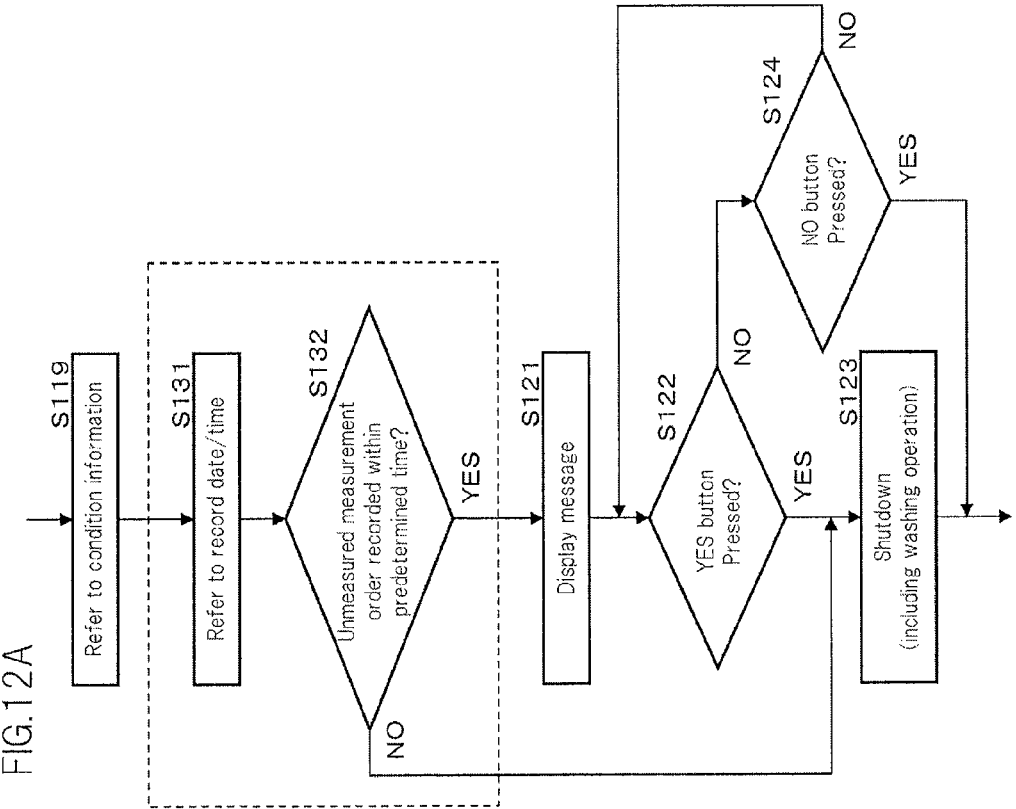

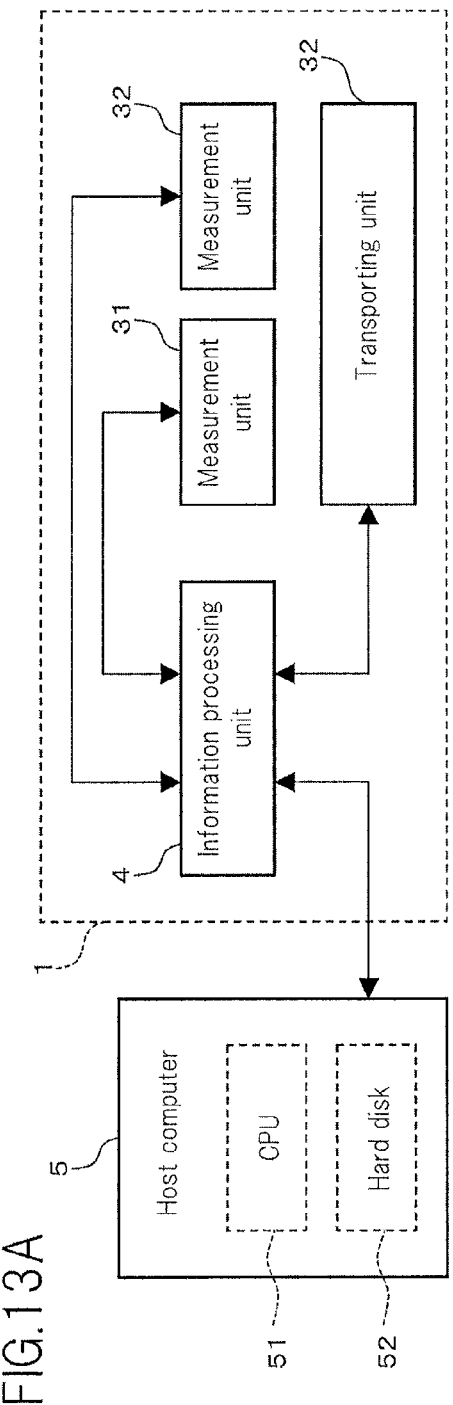
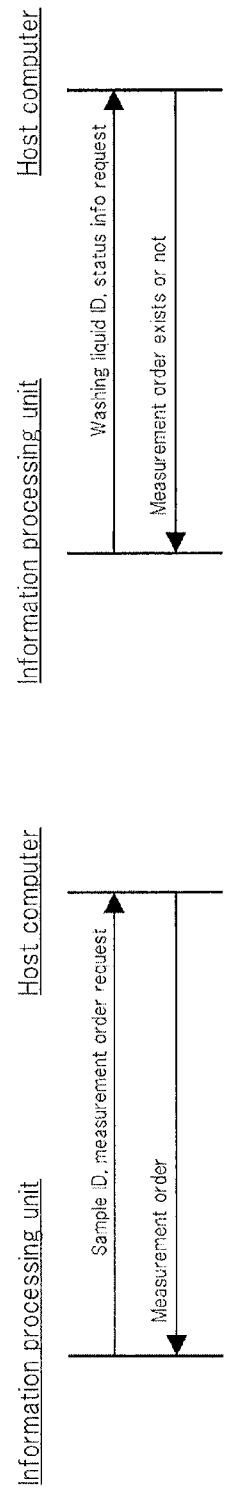
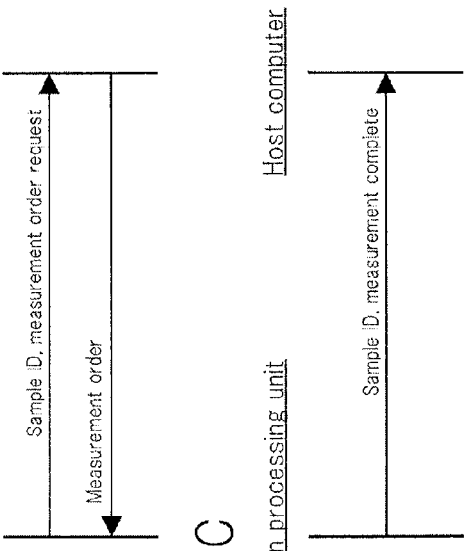
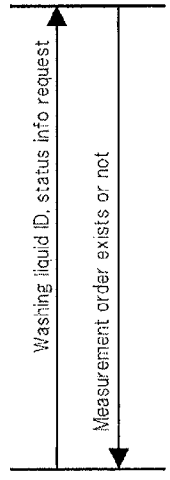
FIG.13A
FIG.13B
FIG.13C
FIG.13D

SAMPLE PROCESSING APPARATUS AND METHOD FOR CONTROLLING A SAMPLE PROCESSING APPARATUS USING A COMPUTER

RELATED APPLICATIONS

This application claims priority under 35 U.S.C. §119 to Japanese Patent Application No. 2011-281604 filed on Dec. 22, 2011, the entire content of which is hereby incorporated by reference.

BACKGROUND OF THE INVENTION

1. Field of the Invention

The present invention relates to a sample processing apparatus for processing clinical samples such as blood and urine.

2. Description of the Related Art

Sample processing apparatuses for aspirating a sample from a sample container with an aspirating tube and processing the aspirated sample are known. When using a sample processing apparatus over a long period, dirt accumulates in the fluid flow system, such as the aspirating tube, flow path, valves, reaction chambers, and analysis unit. Therefore, washing of the fluid flow system is performed during the shutdown operation of the sample processing apparatus. When the fluid flow system washing operation is completed, the power source of the apparatus automatically turns OFF.

Japanese Laid-Open Patent Publication No. 2003-254980 discloses a specimen analyzer that washes the fluid flow system by aspirating a washing liquid from a washing liquid container. In this apparatus, washing of the fluid flow system is performed by moving a rack holding the washing liquid container to an aspirating position, and aspirating the washing liquid from the transported washing liquid container with an aspiration part.

The washing of the fluid flow system requires a lengthy time to complete washing because washing liquid must be retained in the flow path. When a lengthy time has elapsed and the washing ends, a shutdown operation is performed to automatically turn OFF the power to the apparatus. After the apparatus is turned OFF, it must be restarted in order to be used. After the shutdown operation has started, therefore, the specimen analyzing apparatus cannot be used for a long time. An operator may initiate the shutdown operation, having forgotten that specimens remain to be measured. In this case, the operator must wait to measure the remaining specimens until restarting the apparatus is completed.

SUMMARY OF THE INVENTION

A first aspect of the present invention is a sample processing apparatus comprising: a sample processing section configured to perform a process on a sample; and a controller configured to execute an order defining a process to be performed on a sample and to cause the sample processing section to perform the process on the sample according to the order, wherein when the controller receives an instruction to perform a shutdown operation, the controller performs the following operations comprising: prohibiting the execution of the shutdown operation if an unexecuted order remains; and causing the sample processing section to perform the shutdown operation if there is no unexecuted order.

A second aspect of the present invention is a sample processing apparatus comprising: a sample processing section configured to perform a process on a sample; and a controller configured to control the sample processing section; wherein the controller: controls the sample processing section according to an order, the order defining the process to be performed; and suspends a performance of a washing operation when an unexecuted order exists when a washing instruction to wash the sample processing section is received.

A third aspect of the present invention is a method of controlling a sample processing apparatus using a computer, comprising steps of: (a) receiving an input of an order defining content of a process to be performed on a sample; (b) receiving an input of identification information of a sample; (c) transmitting a command to perform a process on the sample to the sample processing apparatus according to an order corresponding to the identification information of the sample; (d) updating a status of the order to executed after completion of the process; (e) receiving a shutdown instruction; and (f) performing step (f-1) if status of all orders received in step (a) is executed, and performing step (f-2) if there is an unexecuted order when an instruction is received in step (e), (f-1) performing the shutdown operation of the sample processing apparatus; (f-2) suspending performing the shutdown operation.

BRIEF DESCRIPTION OF THE DRAWINGS

FIG. 2C is a perspective view showing the rack structure;

FIG. 2D shows the deployment rule for the washing liquid containers;

FIG. 4A is a flow chart showing the sample container take-up operation performed by the measurement unit of the embodiment;

FIG. 4B is a flow chart showing the washing liquid container take-up operation performed by the measurement unit of the embodiment;

FIG. 8 shows an order input screen;

FIGS. 12A and 12B are flow charts showing the control operation of an information processing unit of a modification;

FIG. 13A shows a structure of the host computer of the modification;

FIG. 13B through 13D illustrate communications between the information processing unit and the host computer;

DETAILED DESCRIPTION OF THE PREFERRED EMBODIMENT

Figure 1:
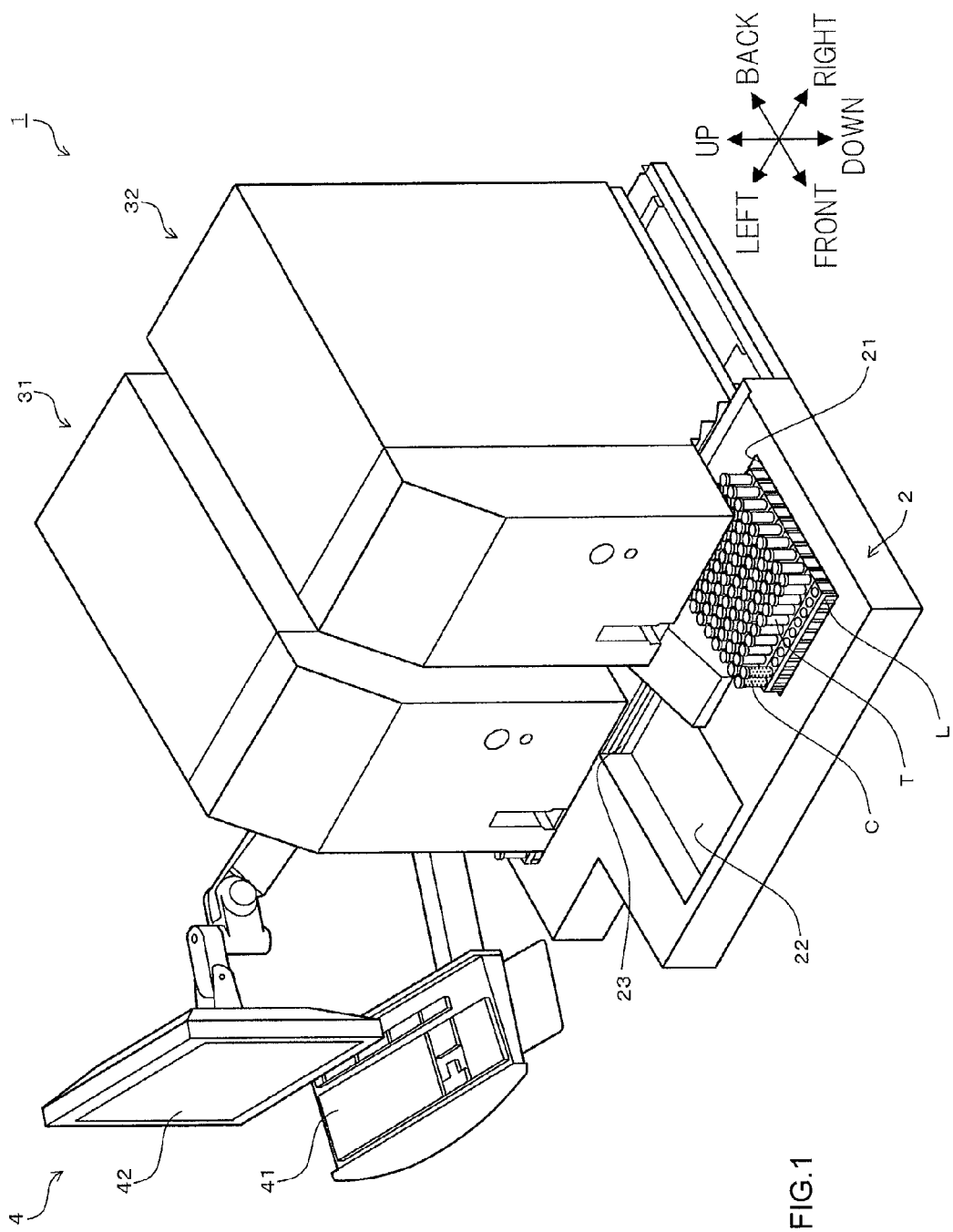
FIG. 1 is an exterior perspective view showing an embodiment of the sample analyzer.

The present embodiment describes the invention by way of an example of a sample analyzer for examining and analyzing a blood sample.

The sample analyzer of the embodiment is described below referring to the drawings.

FIG. 1 is an exterior perspective view of a sample analyzer 1. The sample analyzer 1 of the present embodiment includes a transporting unit 2, measurement units 31, 32 composed of blood cell counters, and information processing unit 4.

The transporting unit 2 is arranged in front of the measurement unit 31 and measurement unit 32. The transporting unit 2 is configured by a right table 21, left table 22, and a rack transporter 23 connecting the right table 21 and the left table 22. The right table 21 and the left table 22 are capable of accommodating a plurality of racks, which are capable of holding ten sample containers T and washing liquid containers C.

The transporting unit 2 can hold a rack L installed on the right table 21 by the operator. The transporting unit 2 transports the sample rack L held on the right table 21 to a predetermined position of the rack transporter 23 to supply the sample containers T and the washing liquid containers C to the measurement unit 31 and the measurement unit 32. The transporting unit 2 then transports the sample rack L on the rack transporter 23 to the left table 22. The rack L is therefore transported so as to move from the right table 21 toward the left table 22. In the following description of the transport path, the direction approaching the right table 21 is referred to as the upstream transport direction, and the direction approaching the left table 22 is referred to as the downstream transport direction.

Figure 3:
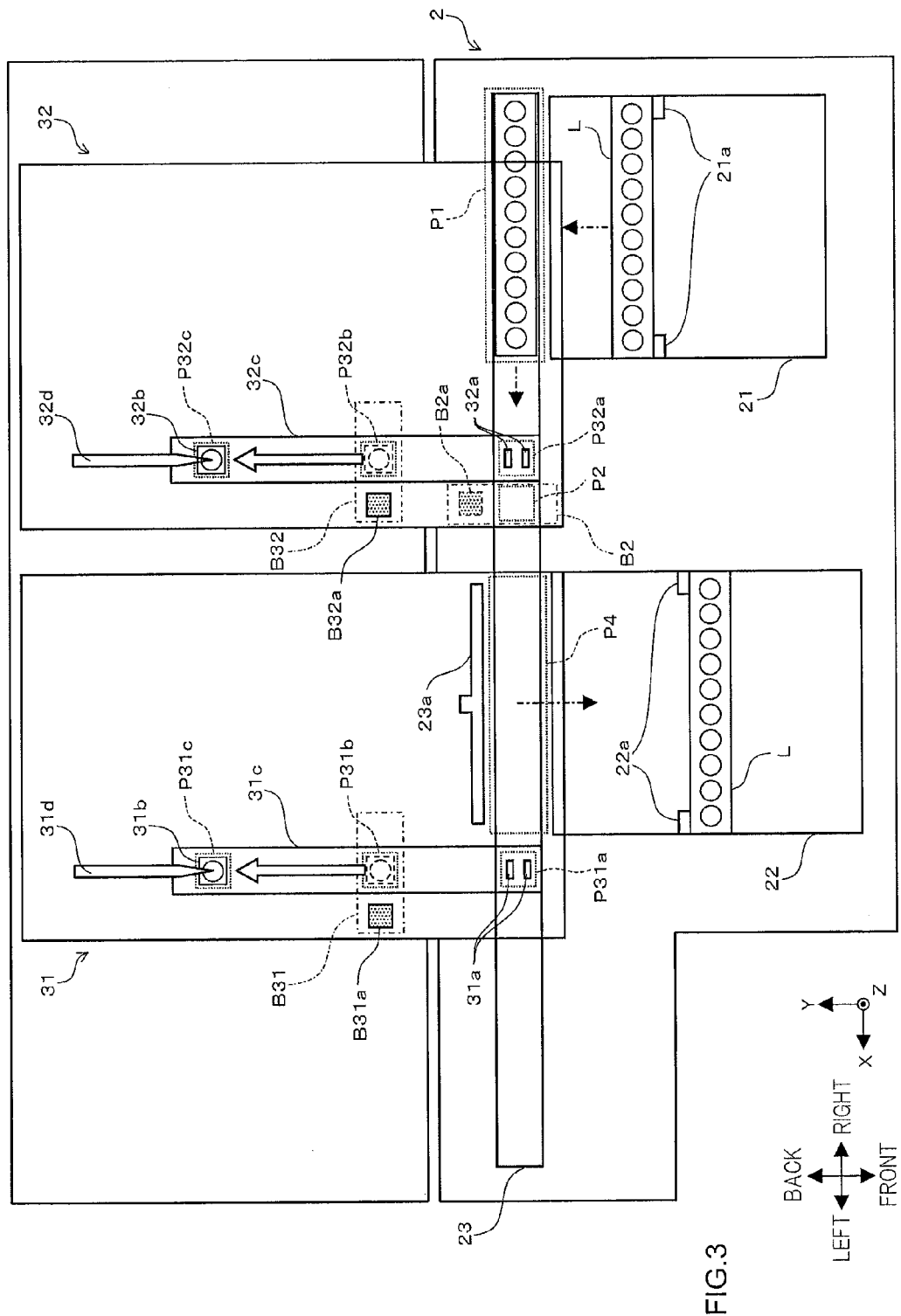
FIG. 3 is a schematic view showing the structures of the transporting unit and measurement unit of the embodiment viewed from above.

In the present embodiment, the container held in the rack L is picked up for processing by the measurement unit 21 or the measurement unit 22 at either the take-up position P31a or P32a on the rack transporter 23 (refer to FIG. 3).

Figure 2A:
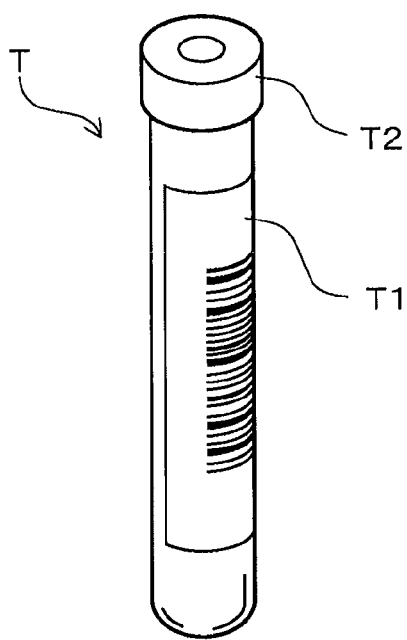
FIG. 2A is an exterior perspective view showing a sample container.
Figure 2B:
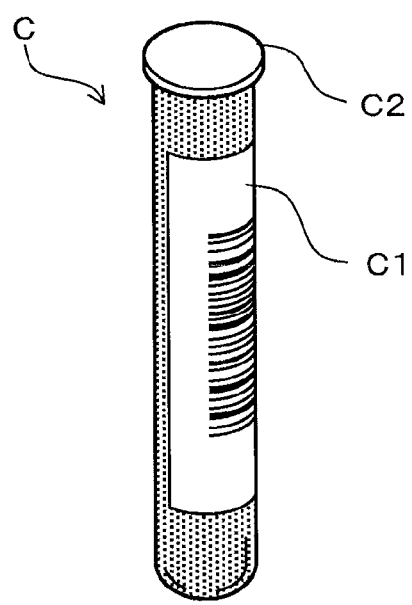
FIG. 2B is an exterior perspective view showing a washing liquid container.

FIGS. 2A, 2B, and 2C shows the structures of the sample container T, washing liquid container C, and the rack L. FIGS. 2A and 2B are exterior perspective views of the sample container T and the washing liquid container C. FIG. 2C is an exterior perspective view of the rack L holding ten sample containers T. Note that FIG. 2C shows the directions (front/back, left/right and upstream/downstream in the transporting direction) when the rack L is placed on the transporting unit 2.

Referring to FIG. 2A, the sample container T is a tube-like container, open at the top end, and formed of transparent synthetic resin or glass. A barcode label T1 is adhered to the side surface of the sample container T. A barcode including the sample ID is printed on the barcode label T1. The sample container T contains a blood sample of whole blood collected from a patient, and the opening at the top end is sealed with a rubber cap T2.

Referring to FIG. 2B, the washing liquid container C is a tube-like container, open at the top end, and formed of colored synthetic resin or glass. The color of the washing liquid container C is different than the color of the sample container T for easy visual identification. The washing liquid container C has the same shape and size as the sample container T.

A barcode label C1 is adhered to the side of the washing liquid container C. A barcode including the washing liquid ID is printed on the barcode label C1, and the washing liquid ID can be discriminated from the sample ID. The washing liquid container C holds a chlorine-based washing liquid for washing the fluid circuit within the measurement unit 31 or measurement unit 32, and the opening on the top end of the container is sealed by a film C2.

Referring to FIG. 2C, a barcode label L1 is adhered to the back side of the rack L. A barcode indicating the rack ID is printed on the barcode label L1. The rack L has holders capable of vertically holding ten sample containers T and washing liquid containers C. For convenience, the position of each holder is referred to by holding positions 1 through 10 arranged in ascending order from the downstream side to the upstream side in the transport direction.

FIG. 2D illustrates the deployment rule of the washing liquid container C on the rack L. FIG. 2D shows the placement of the washing liquid container C when the rack L is viewed from above. FIG. 2D shows both the numbers of the holding positions of the rack L shown in FIG. 2C and the downstream-upstream transport direction.

When washing both the measurement units 31 and 32, the operator sets the washing liquid containers C in holder positions 1 and 2, and does not set either the sample containers T or washing liquid containers C in the other holding positions, as shown at the upper level of FIG. 2D. In this case, the washing liquid container C of holding position 1 is allocated to the measurement unit 31, and the washing liquid container C of the holding position 2 is allocated to the measurement unit 32.

When only washing the measurement unit 31, the operator sets the washing liquid container C only in holder position 1, and does not set either the sample containers T or washing liquid containers C in the other holding positions, as shown in the mid level of FIG. 2D. In this case, the washing liquid container C of the holding position 1 is allocated to the measurement unit 31. When only washing the measurement unit 32, the operator sets the washing liquid container C only in holder position 2, and does not set either the sample containers T or washing liquid containers C in the other holding positions, as shown in the lower level of FIG. 2D. In this case, the washing liquid container C of the holding position 2 is allocated to the measurement unit 32.

Hence, when washing the measurement unit 31 and the measurement unit 32, the washing liquid container C may be placed in either holding position 1 or holding position 2, or both, of the rack L.

Returning now to FIG. 1, during measurement of a sample, the measurement unit 31 performs processing of the sample container C on the rack transporter 23 in front of the measurement unit 31. That is, the measurement unit 31 removes the sample container T from the rack L via the hand part 31a (refer to FIG. 3) at the take-up position P31a (refer to FIG. 3) of the rack transporter 23, and moves the sample container T into the measurement unit 31, and the sample within the sample container T then is aspirated in the measurement unit 31. When the aspiration is completed, the measurement unit 31 returns the sample container T back to the original holder of the sample rack L. The measurement unit 32 aspirates samples in the same way as the measurement unit 31.

During washing, the measurement unit 31 performs a process regarding the washing liquid container C on the rack L disposed in front of the measurement unit 31. That is, similar to when measuring the sample container T, the measurement unit 31 removes the washing container C from the rack L by the hand part 31a (refer to FIG. 3) at the take-up position P31a (refer to FIG. 3) of the rack transporter 23, and moves the washing liquid container C into the measurement unit 31. The measurement unit 31 then aspirates the washing liquid held in the washing liquid container C. The measurement unit 31 injects the washing liquid into the detection part and the flow path used in the measurement of the sample, and washing liquid is allowed to stand a predetermined time to clean.

The washing process is performed once per day. To avoid residual soiling caused by previous sample measurements, the washing liquid is allowed to stand for a long time to clean the flow path, detection part and the like.

When the aspiration of the washing liquid is completed, the measurement unit 31 returns the washing liquid container T back to the original holder of the sample rack L. The measurement unit 32 aspirates washing liquid in the same way as the measurement unit 31. The washed measurement units 31 and 32 then have the power source turned OFF, or enter a standby state according to the set mode which will be described later. Hence, the measurement unit 31 and the measurement unit 32 complete shutdown by having the power source turned OFF after washing, or entering a standby state after washing.

The information processing unit 4 has an input part 41 and a display part 42. The information processing unit 4 is connected via a communication network so as to be capable of communicating with the transporting unit 2, measurement unit 31, and measurement unit 32. The information processing unit 4 controls the operation of the transporting unit 2, the measurement unit 31, and measurement unit 32, and performs analysis based on the measurement results of the measurement units 31 and 32. The information processing unit 4 also shows messages on the display part 42.

FIG. 3 is a schematic view showing the structures of the transporting unit 2, measurement unit 31, and measurement unit 32 viewed from above.

The barcode information reading operation is described first referring to FIG. 3.

The rack L loaded in the right table 21 is moved to the feed position P1 on the right end of the rack transporter 23 by the rack mover 21a pushing the front side of the rack L. The rack L placed at the feed position P1 is then moved leftward by a belt (not shown in the drawing) of the rack transporter 23. Note that there are two belts of the rack transporter 23 arranged side by side in the front-to-back direction, so that the racks L can be moved in lateral directions by each belt when two racks L are positioned on the rack transporter 23.

A barcode unit B2 with a barcode reader B2a is installed near the center of the rack transporter 23. When the holder of the rack L is set at the reading position P2 in front of the barcode reader B2a, a determination is made as to whether a container (either a sample container T or a washing liquid container C) is held in the holder by a hold determining device (not shown in the drawing) of the barcode unit B2. The hold determining device is configured by a mechanism capable of grasping a container from the front-to-back direction (Y-axis direction). When a container can be gripped by the mechanism, it is determined that a container is held in the holder set at the reading position P2.

When a sample container T is held in the holder, the sample ID is read from the barcode label T1 of the sample container T by the barcode reader B2a as the sample container T is rotated. When a washing liquid container C is held in the holder, the washing liquid ID is read from the barcode label C1 of the washing liquid container C by the barcode reader B2a as the washing liquid container C is rotated. When the barcode label L1 of the rack L is positioned in front of the barcode reader B2a, the rack ID is also read from the barcode label L1 of the rack L by the barcode reader B2a.

Hence, the barcode information of the rack L, the information of the presence of a container in all ten holders at holder positions 1 through 10 of the rack L, and the barcode information of the containers held in the rack L are obtained.

The operations for supplying the sample container T and the washing liquid container C of the rack L to the measurement units 31 and 32 are described below.

In general, when reading the barcode information as described above, the sample containers T in the holders of the rack L are alternatingly supplied sequentially to the measurement unit 31 and measurement unit 32 in sequence from the container at the downstream (left direction) holding position in the transporting direction. For example, when sample containers T are present in holding positions 1 through 3 of the rack L, the sample container T at holding position 1 is set at the take-up position P31a of the measurement unit 31. The hand part 31a is installed in the measurement unit 31 so as to be movable in vertical directions (Z-axis direction) at the take-up position P31a. The sample container T set at the take-up position P31a is gripped by the hand part 31a and removed in an upward direction (Z-axis positive direction) from the rack L, and placed into the measurement unit 31.

After the sample container T of holding position 1 has been retrieved by the measurement unit 31, the sample container T of the holding position 2 is set at the take-up position P32a of the measurement unit 32. The sample container T set at the take-up position P32a is gripped by the hand part 32a and removed in an upward direction (Z-axis positive direction) from the rack L, and placed into the measurement unit 32.

Thereafter, when the measurement is completed for the sample in the sample container T of the holding position 1 in the measurement unit 31, the holding position 1 is again set at the take-up position P31a of the measurement unit 31. The sample container T held by the hand part 31a of the measurement unit 31 is set in the holding position 1 of the rack L from above (Z-axis positive direction).

Hence, the measurement unit 31 becomes empty and the sample container T of the holding position 3 is set at the take-up position 31a of the measurement unit 31 and then moves into the measurement unit 31.

Supplying the washing liquid container C to the measurement units 31 and 32 is conducted according to the deployment rule shown in FIG. 2D. For example, when the washing liquid container C is placed as shown in the upper level of FIG. 2D, the washing liquid container C of holding position 1 and the washing liquid container C of holding position 2 are sequentially set at the take-up positions P31a and P32a, respectively. The two washing liquid containers C are placed in the measurement units 31 and 32, respectively. The washing liquid containers are thus placed in the measurement unit corresponding to the holding position of the rack. When the washing liquid container C is set as shown in the mid level of FIG. 2D, the washing liquid container C of the holding position 1 is therefore placed in the measurement unit 31. When the washing liquid container C is set as shown in the lower level of FIG. 2D, the washing liquid container C of the holding position 2 is therefore placed in the measurement unit 32.

FIG. 4A is a flow chart showing the sample container T take-up operation of the measurement units 31 and 32. The sample container T take-up operation performed by the measurement unit 31 is described as representative of the measurement units 31 and 32.

When the sample container T is set at the take-up position P31a of the measurement unit 31, the sample container T is gripped by the hand part 31a and removed in an upward direction (Z-axis positive direction) (S31). The hand part 31a moves the sample container T in a pendulum-like fashion to stir the sample (S32). The container receiver 31b moves forward (Y-axis negative direction) above the take-up position P31a so that the container receiver 31b is positioned beneath the hand part 31a (S33). After stirring, the hand part 31a is moved downward (Z-axis negative direction) and the sample container T is set on the container receiver 31b.

Thereafter, the container receiver 31b is moved backward (Y-axis positive direction) to the barcode reading position P31b (S35), the presence of the sample container T is recognized and the barcode is again read by the barcode unit B31 provided with the barcode reader B31a (S36). Note that the barcode unit B31 is provided with a hold determining device (not shown in the drawing) identical to the barcode unit B2.

The container receiver 31b is then set at the aspirating position P31c directly below the pipette 31d (S37). The pipette 31d then is moved downward and pierces the cap on the sample container T positioned at the aspirating position P31c, and aspirates the sample within the sample container T (S38).

When the aspiration of the sample by the pipette 31d ends, the container receiver 31b is moved forward and set again at the take-up position P31a (S39). At the take-up position P31a, the sample container T is moved upward from the container receiver 31b by the hand part 31a. The container receiver 31b is moved backward and the hand part 31a is moved downward (Z-axis negative direction) to return the sample container T to the holder of the rack L positioned in the rack transporter 23 (S41).

FIG. 4B is a flow chart showing the washing liquid container C take-up operation by the measurement unit 31 and measurement unit 32.

S51 and S52 through S60 in FIG. 4B are comparable to S31 and S33 through S41 of FIG. 4A, but the sample container T is replaced by the washing liquid container C. Hence, the description of each step is abbreviated. In the take-up operation of FIG. 4B, the step corresponding to S32 of FIG. 4A is omitted. This step is omitted inasmuch as the stirring operation is unnecessary since the container is the washing liquid container C.

After washing liquid has been aspirated from all the washing liquid containers C, the rack L is positioned at the rear position on the left table 22, and is moved forward on the left table 22 by the rack mover 22a.

Figure 5:
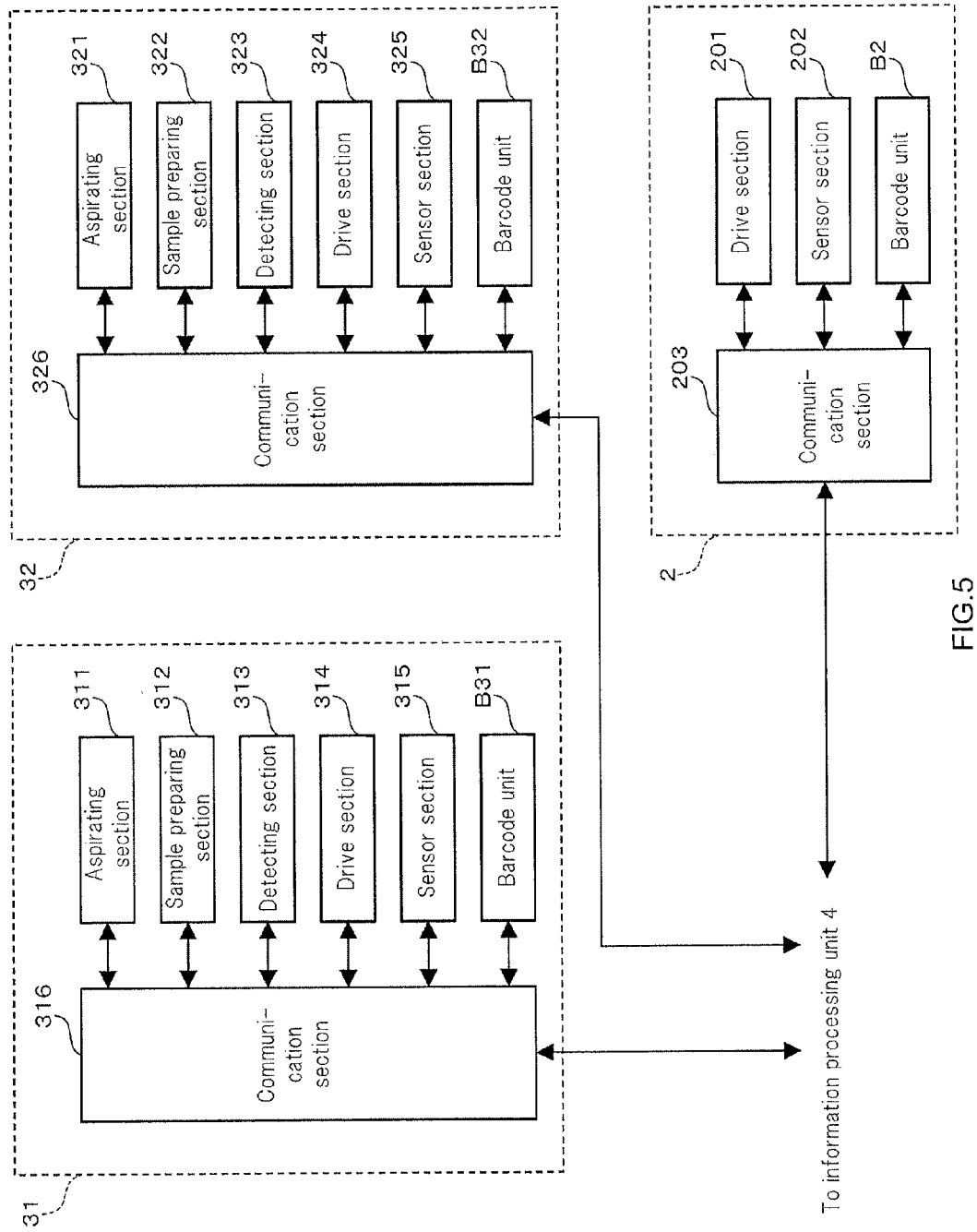
FIG. 5 is a block diagram showing a structure of the transporting unit and the measurement unit of the embodiment.

FIG. 5 shows the structures of the transporting unit 2, measurement unit 31 and measurement unit 32.

The transporting unit 2 has a drive section 201, sensor section 202, barcode unit B2, and communication section 203.

The drive section 201 includes a device for moving the rack L within the transporting unit 2, and the sensor section 202 includes sensors for detecting the rack L on the transport path of the transporting unit 2. The barcode unit B2 includes a hold determining device (not shown in the drawing), and a barcode reader B2a, as described above.

The communication section 203 is connected to the information processing unit 4 and is capable of communication therewith. Each section of the transporting unit 2 is controlled by the information processing unit 4 through the communication section 203. Signals output from the various sections in the transporting unit 2 are also transmitted to the information processing unit 4 through the communication section 203.

The measurement unit 31 has an aspirating section 311, sample preparing section 312, detecting section 313, drive section 314, sensor section 315, barcode unit B31, and communication section 316. The measurement unit 32 has an aspirating section 321, sample preparing section 322, detecting section 323, drive section 324, sensor section 325, barcode unit B32, and communication section 326.

Since the measurement unit 31 and the measurement unit 32 have completely identical structures, only measurement unit 31 is described below.

Figure 6:
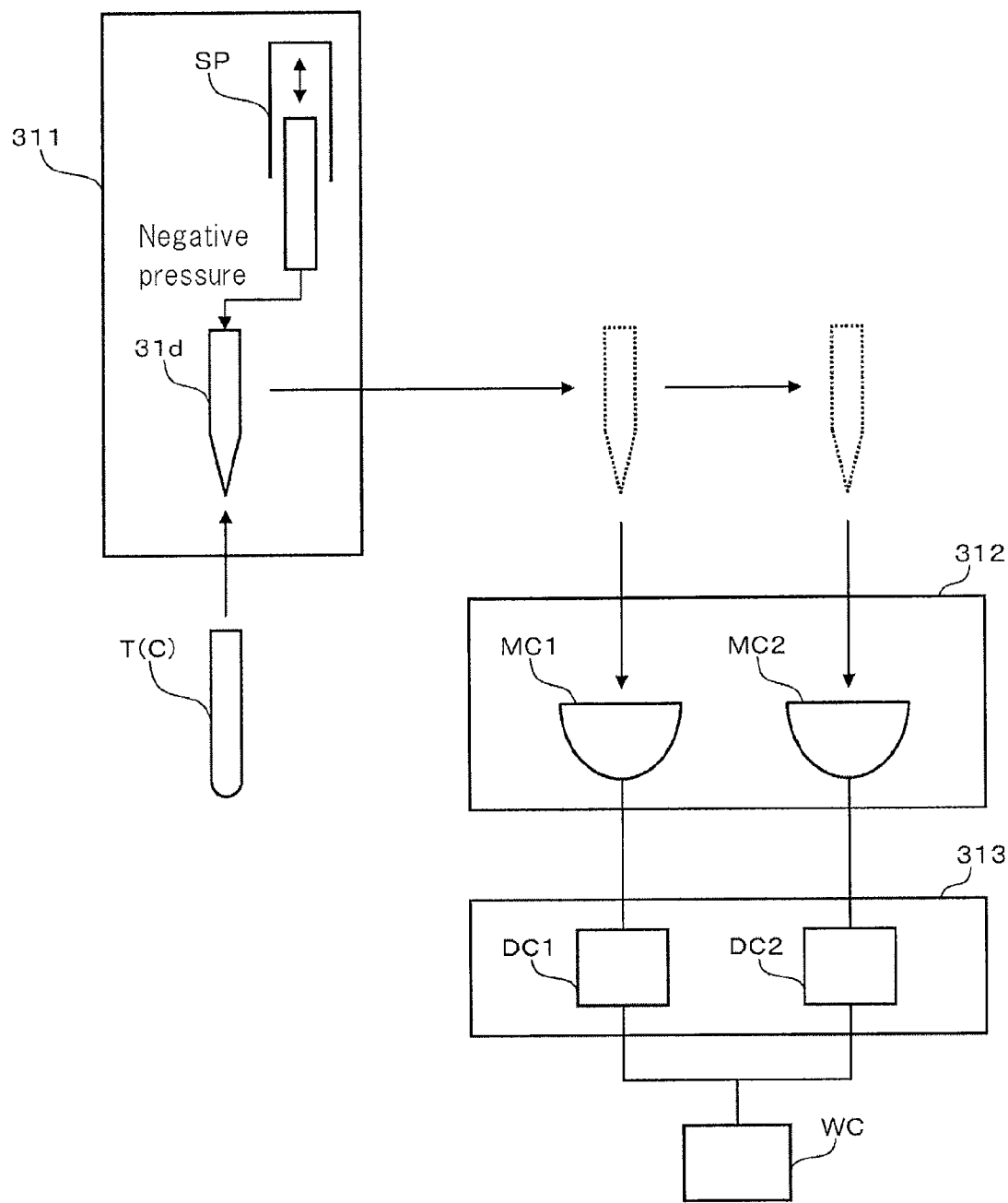
FIG. 6 shows a structure of the fluid flow circuit of the measurement unit of the embodiment.

FIG. 6 shows the structure of the fluid flow circuit of the measurement unit 31.

The aspirating section 311 includes an aspirating pipette 31d for piercing a sealing of the containers and aspirating sample from the sample container T and washing liquid from the washing liquid container C that have been moved into the measurement unit 31, and a syringe pump SP for exerting a negative pressure on the pipette 31d. The tip of the pipette 31d is sharp to puncture and pierce the cap C2 of the washing liquid container C and the cap T2 of the sample container T. The sample preparing section 312 has a reaction chamber MC1 for preparing samples for measuring red blood cells and platelets, and a reaction chamber MC2 for preparing samples for measuring white blood cells. The detecting section 313 has an electrical resistance type detector DC1 for measuring red blood cells and platelets, and optical type detector DC2 for optically measuring white blood cells. The measurement unit 31 also has a waste fluid chamber WC for storing waste fluids.

When measuring a sample contained in a sample container T, the aspirating section 311 aspirates the sample through the pipette 31d by causing the syringe pump SP to exert a negative pressure on the pipette 31d. The pipette 31d discharges the aspirated sample to the reaction chamber MC1 and reaction chamber MC2. The sample preparing section 312 stirs and mixes the sample and reagent within the reaction chamber MC1 to prepare a sample to be used for measuring red blood cells and platelets. The sample preparing section 312 also stirs and mixes the sample and reagent within the reaction chamber MC2 to prepare a sample for measuring white blood cells. The sample prepared in the reaction chamber MC1 is moved to the electrical resistance type detector DC1 through a flow path, and the sample prepared in the reaction chamber MC2 is moved to the optical type detector DC2 through a flow path. The detecting section 313 detects the optical information (side fluorescent light signals, forward scattered light signals, and side scattered light signals) from the white blood cells and nucleated red blood cells in the sample as sample data via the optical type detector DC2. The detecting section 313 also detects the electrical information from the red blood cells and platelets in the sample as sample data via the electrical resistance type detector DC1. The samples that have passed through the detecting section 313 are then moved to the waste liquid chamber WC through a flow path.

When washing using the washing liquid contained in the washing liquid container C, the washing liquid flows through the same flow path as the sample. That is, the flow path from each reaction chamber to the waste liquid chamber WC is filled with washing liquid by aspirating the washing liquid from the washing liquid container C and discharging the aspirated washing liquid into each reaction chamber of the sample preparing section 312 by the aspirating section 311. The residue of sample and reagent adhered to the inner walls of each reaction chamber are removed therefrom by being filled with the washing liquid for a long time.

Returning to FIG. 5, the drive section 314 includes a mechanism to transport the sample container T and the washing liquid container C within the measurement unit 31. The sensor section 315 includes sensors to detect the sample container T and the washing liquid container C at predetermined positions on the transport path within the measurement unit 31. The barcode unit B31 includes a hold determining device (not shown in the drawing), and a barcode reader B31a, as described above.

The communication section 316 is connected to the information processing unit 4 and is capable of communication therewith. Each section of the measurement unit 3 is controlled by the information processing unit 4 through the communication section 316. Signals output from the various sections in the measurement unit 3 are also transmitted to the information processing unit 4 through the communication section 316.

Figure 7:
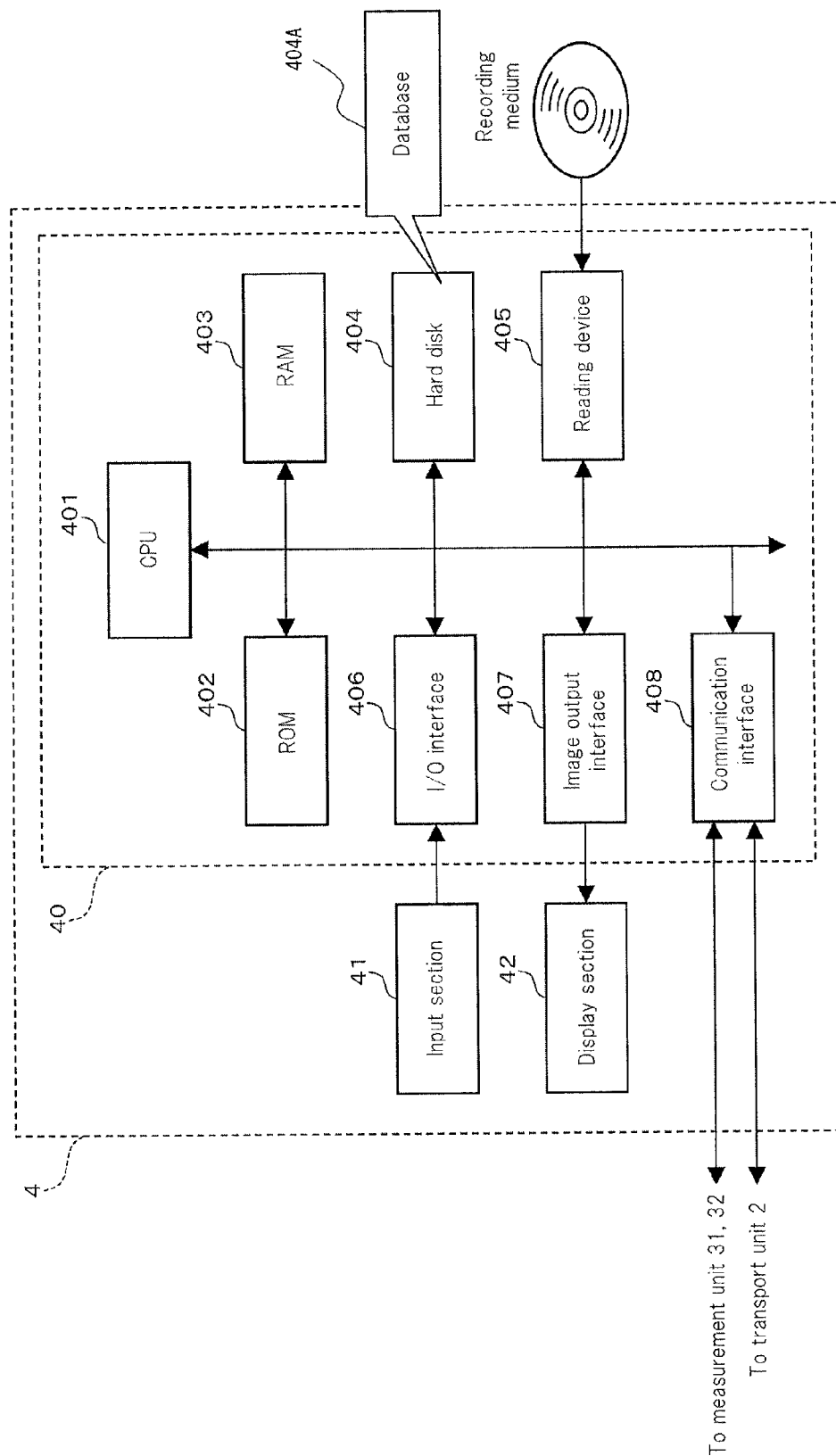
FIG. 7 shows a structure of the information processing unit of the embodiment.

FIG. 7 shows the structure of the information processing unit 4.

The information processing unit 4 is configured by a personal computer having a main body 40, input section 41, and display section 42. The main body 40 has a CPU 401, ROM 402, RAM 403, hard disk 404, reading device 405, I/O interface 406, image output interface 407, and communication interface 408.

The CPU 401 is capable of executing a computer program stored in the ROM 402 and a computer program loaded in the RAM 403. The RAM 403 is used when reading the computer program stored in the ROM 402 and recorded on the hard disk 404. The RAM 403 is also used as the work area of the CPU 401 when the CPU 401 executes the computer programs.

An operating system and application programs, as well as the data used when executing the operating system and application programs that are executed by the CPU 401, are installed on the hard disk 404. That is, the hard disk 404 stores programs for analyzing the sample data transmitted from the measurement units 31 and 32 and generating measurement results such as the red blood cell count and white blood cell count, and showing results on the display section 42 based on the generated measurement results.

A database 404A for associating and storing measurement orders (described later), recording date and time information, and status information is also stored on the hard disk 404. Measurement orders are information including various items as well as the sample ID, and measurement items associated with the sample ID. The recording date and time is information representing the date and time the measurement order was recorded, and is stored in memory associated with each measurement order. The status information is information indicating whether the measurement was completed based on the measurement order, and is stored in memory associated with each measurement order.

The reader 405 is a CD drive or DVD drive capable of reading computer programs and data recorded on a recording medium. The I/O interface 406 is connected to the input section 41 configured by a mouse and keyboard, and the user uses the input section 41 to input instructions and data to the information processing unit 4. The image output interface 407 is connected to the display section 42 configured by a display of some type, and the image output interface 407 outputs image signals corresponding to the image data to the display 42.

The display section 42 displays images based on the input image signals. Various types of program screens are shown on the display section 42. Data transmission and reception is possible with the transporting unit 2, measurement unit 31, and measurement unit 32 through the communication interface 408.

Figure 8:
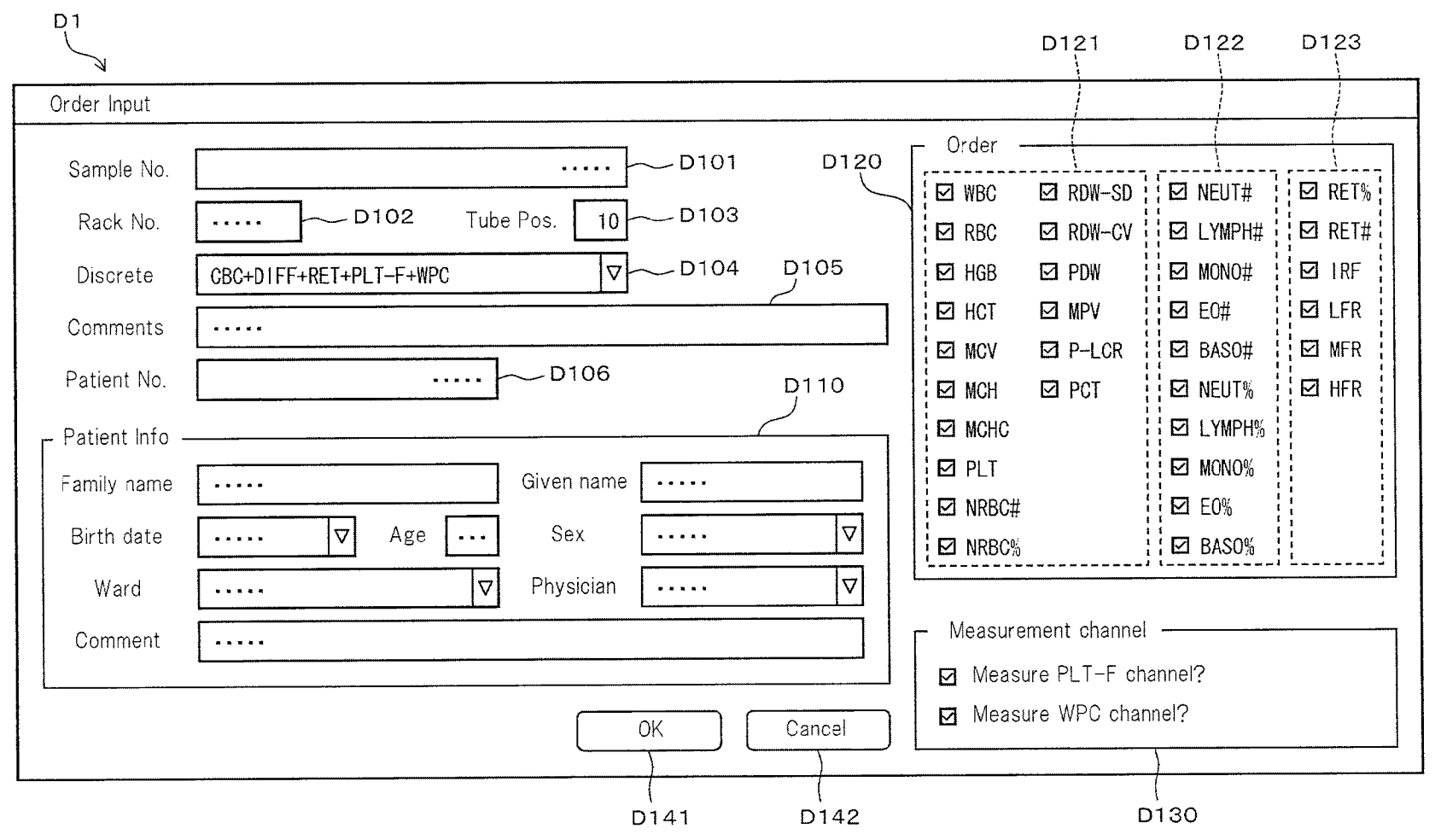

FIG. 8 shows an order input screen D1 being displayed on the display section 42 of the information processing unit 4.

The order input screen D1 includes a sample number input field D101, rack number input field D102, test tube position input field D103, discrete selection field D104, sample comment input field D105, patient number input field D106, patient information input region D110, order selection region D120, measurement channel selection region 130, and buttons D141 and D142. The operator can show the order input screen D1 on the display section 42 by operating the input section 41 of the information processing unit 4.

The sample number input field D101 is an input box for entering the sample ID included in the barcode label T1 of the sample container T. The rack number input field D102 is an input box for entering the rack ID included in the barcode label L1 of the rack L. The test tube position input field D103 is an input box for entering the hold position of the sample container T. The discrete selection field D104 is a selection box for selecting the combination of measurement items prepared in advance from among the measurement items (discrete). When selecting a measurement item combination in the discrete selection field D104, selection of a checkbox included the order selection region D120 and the measurement channel selection region D130 is performed. The sample comment field D105 and patient number input field D106 are input boxes for entering comments of the sample and the number of the patient from whom the sample was collected.

The patient information input region D110 includes a selection box and input box for selecting and entering various information of the patient from whom the sample was collected.

The order selection field D120 includes a CBC field D121, DIFF field D122, and RET field D123, and is a region for detailed setting of measurement items for a sample. The CBC field D121, DIFF field D122, and RET field D123 include checkboxes for selecting measurement items included in the CBC item, DIFF item, and RET item, respectively. The measurement channel selection region D130 includes checkboxes for selecting two measurement items. Note that when an operator designates a specific combination of measurement items from the order selection region D120 and the measurement channel selection region D130, the display of the discrete selection field D104 becomes "Free Selection."

When the button D141 is pressed, input and selected items in the order input screen D1 are stored on the hard disk 404 of the information processing unit 4. When the button D142 is pressed, the input and selected items within the order input screen D1 are deleted. Hence, the operator can set various items including measurement items to be performed on the sample associated with the sample ID through the order input screen D1 shown in FIG. 8. Items set through the order input screen D1 are referred to as "measurement order" hereinafter.

When the button D141 is pressed and the measurement order is stored in memory, the date and time when the button D141 is pressed (record date and time information) is associated with the sample ID and stored on the hard disk 404. When the button D141 is pressed and the measurement order is stored, the information indicating whether the measurement has been completed based on the measurement information (hereinafter referred to as "status information") is associated with the sample ID and stored on the hard disk 404. The content of the status information is either "unmeasured" or "completed". The status information is set by default to "unmeasured" when the measurement order is recorded.

Figure 9:
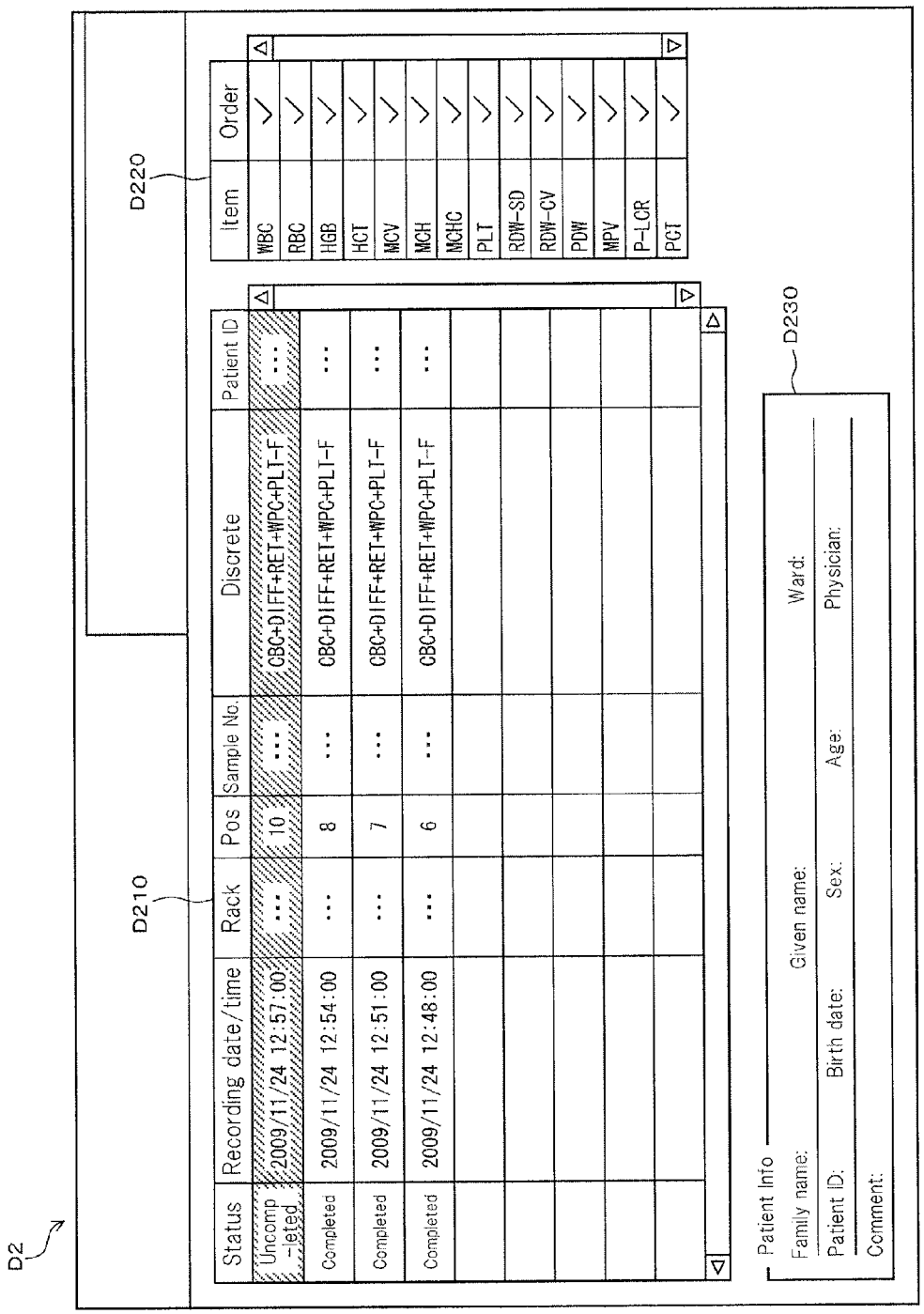
FIG. 9 shows a measurement record screen.

FIG. 9 shows a measurement record screen D2 being displayed on the display section 42 of the information processing unit 4.

The measurement record screen D2 includes an order list region D210, an order region D220, and a patient information region D230.

The measurement orders stored on the hard disk 404 through the order input screen D1 are shown in the form of a list in the order list region D210. Specifically, the rack item representing the rack ID, position item representing the test tube position, the sample number item representing the sample ID, discrete item representing the measurement items, and the patient ID item representing the patient ID are shown among the measurement orders. Other items are shown through the side scroll bar of the order list region D210.

The status item representing the status information associated with the sample ID, and the recording date/time item representing the recording date and time information associated with the sample ID are shown in the order list region D210. Status information content ("unmeasured" or "completed") is displayed in the status items, and recording date/time information content (year/month/day and time) is displayed in the recording date/time items. Hence, the status item and the recording date/time item of the measurement order corresponding to a single sample ID are displayed together in the order list region D210.

Details of the discrete item of the measurement order selected in the order list region D210 is shown in the order region D220. All measurement items in the order selection region D120 and the measurement channel selection region D130 of FIG. 8 are shown among the items of the order region D220. Order items of the order region D220 are displayed with a check mark indicating whether to perform the measurement relative to the measurement items shown among the items. Note that the order region D220 shown in FIG. 9 allows the display content to be moved vertically via the vertical scroll bar.

Patient information of the measurement order selected by the order list D210 is shown in the patient information region D230. The patient information region D230 corresponds to each item included in the patient information input region D110 of FIG. 8.

The operator can verify the content of the measurement order stored on the hard disk 404 by referring to the measurement record screen D2 shown FIG. 9. The operator can be informed of the date and time recorded in the measurement order, and whether the sample measurement has been performed based on the measurement order by referring to the status item and the recording date/time item of the order list region D210.

Figure 10:
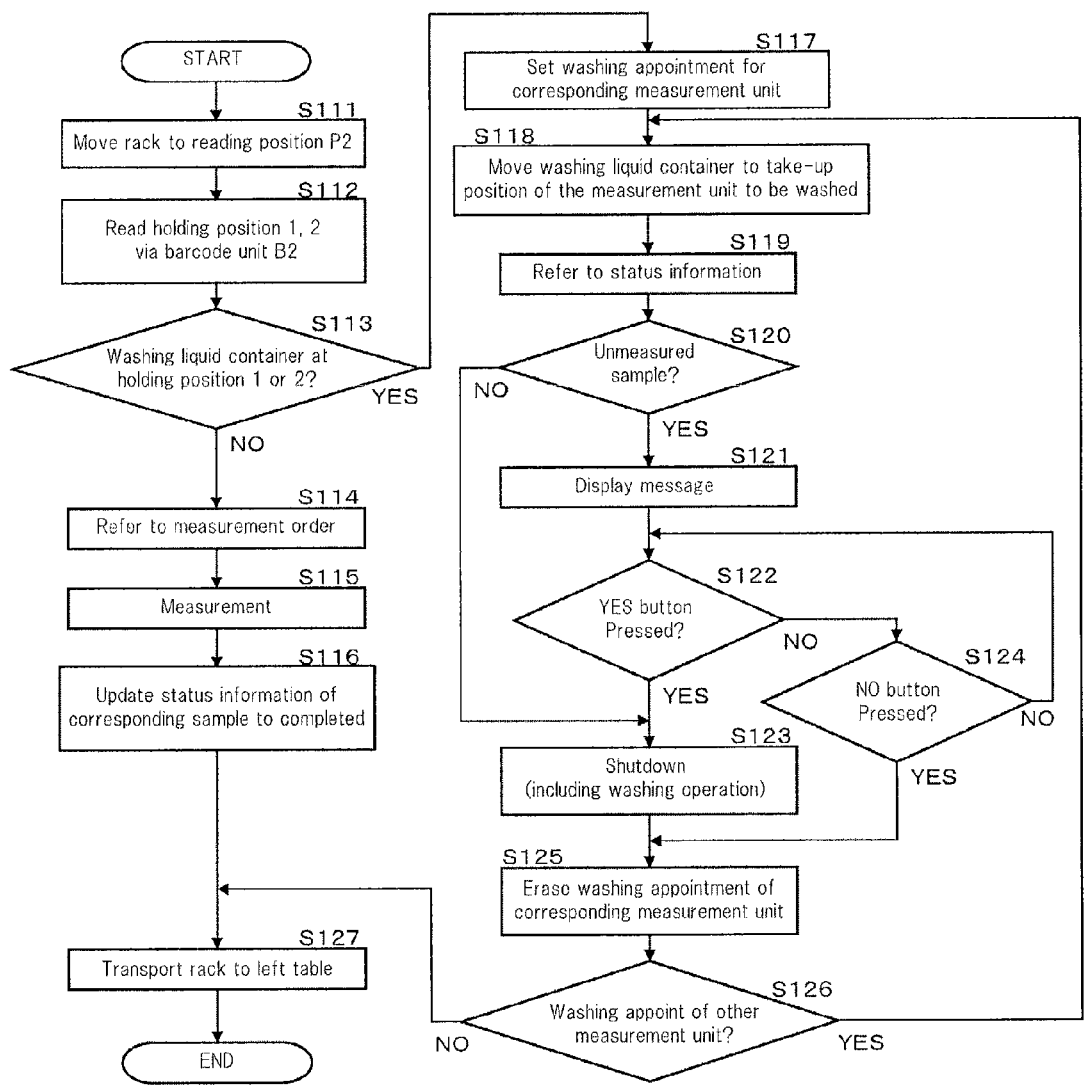
FIG. 10 is a flow chart showing a control operation by the information processing unit of the embodiment.

FIG. 10 is a flow chart showing the transport control of the rack L. Note that the operation of each section mentioned below is realized by the CPU 401 of the information processing unit 4 transmitting commands to each section according to an algorithm shown in the flow chart.

The transporting unit 2 moves the rack L disposed on the right table 21 to the reading position P2 of the barcode unit B2 (S111). The barcode unit B2 then reads the barcode of the containers held at holding position 1 and 2 of the rack L (S112). More specifically, the barcode information is read from the container when a determination is made as to whether a container is held at the holding position 1 and 2, and a container is determined to be present. Hence, the CPU 401 determines whether the container is a sample container T or washing liquid container C.

When the CPU 401 determines that a washing liquid container T is not held in either the holding position 1 or 2 by the reading performed by the barcode unit B2 (S113: NO), the barcode unit B2 then reads the barcode information from the containers at the holding positions 3 through 10. The measurement units 31 and 32 then perform sequential measurements of the samples of each container (S114 through S116). Note that in this case measurement is only performed for samples of the sample containers T and the washing liquid container C is ignored even if a washing liquid container C is set at a holding position 3 through 10.

The CPU 104 retrieves the corresponding measurement order from the measurement order database 404A stored on the hard disk 404 using the sample ID read from the sample container T as a key (S114). The measurement unit 31 (or 32) performs measurements by moving the sample container T into the measurement unit according to the take-up operation of FIG. 4A (S115). When the measurement of the sample is completed, the CPU 401 updates the content of the status information from "unmeasured" to "completed" in the measurement order corresponding to the sample ID of the sample just measured (S116). Then, when the measurement process ends for all samples held in the rack L, the transporting unit 2 moves the rack L to the left table 22 (S127).

When the CPU 401 determines that a washing liquid container C is held in either the holding position 1 or holding position 2 by the reading performed by the barcode unit B2 (S113: YES), the CPU 401 sets a washing appointment for the corresponding measurement unit according to the deployment rule shown in FIG. 2D (S117). For example, a washing appointment is set for both the measurement units 31 and 32 when a washing liquid container C is set at both holding positions 1 and 2, and a washing appointment is set for only one or another of the measurement units 31 and 32 when a washing liquid container C is set at only holding position 1 or holding position 2.

The transporting unit 2 then moves the rack L to place the washing liquid container C at the take-up position of the measurement unit with the washing appointment (S118). For example, when a washing appointment is set for both the measurement unit 31 and the measurement unit 32, the washing liquid container C at the holding position 1 is moved to the take-up position P31a of the measurement unit 31, and the washing liquid container C at the holding position 2 is moved to the take-up position P32a of the measurement unit 32. When a washing appointment is set for only one of the measurement units 31 or 32, the washing liquid container C at either the holding position 1 or 2 is moved to one or another of the take-up positions P31a or P32a.

Note that when the washing liquid container C is set at the take-up position of the destination measurement unit, the transporting unit 2 stops the transport of the washing liquid container C. That is, the transporting unit 2 moves the washing liquid container C to the take-up position according to the washing appointment set in S117, and if any uncompleted measurement order remains, the washing liquid container C remains at the take-up position until an operation is performed in a message dialog D3, which is described later.

Figure 11A:
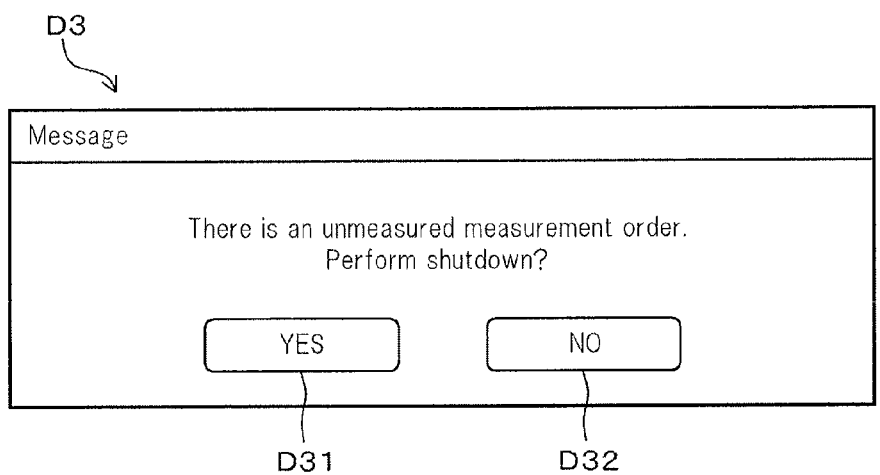
FIG. 11A shows an example of a message dialog.

The CPU 401 then refers to the status information stored in the database 404A on the hard disk 404 (S119). The database 404A stores information regarding whether measurement has been completed ("unmeasured" or "completed") based on each measurement order as the status information, as shown in FIG. 9. When the CPU 401 determines that the measurement order is "unmeasured" (S120: YES) as a result of referring to the status information, the execution of the shutdown operation is temporarily stopped (deferred), and the message dialog D3 shown in FIG. 11A is shown in the display section 42 (S121). Alternatively, when the CPU 401 determines the measurement order is not "unmeasured" (S120: NO), the process advances to S123.

FIG. 11A shows the message dialog D3.

Figure 11B:
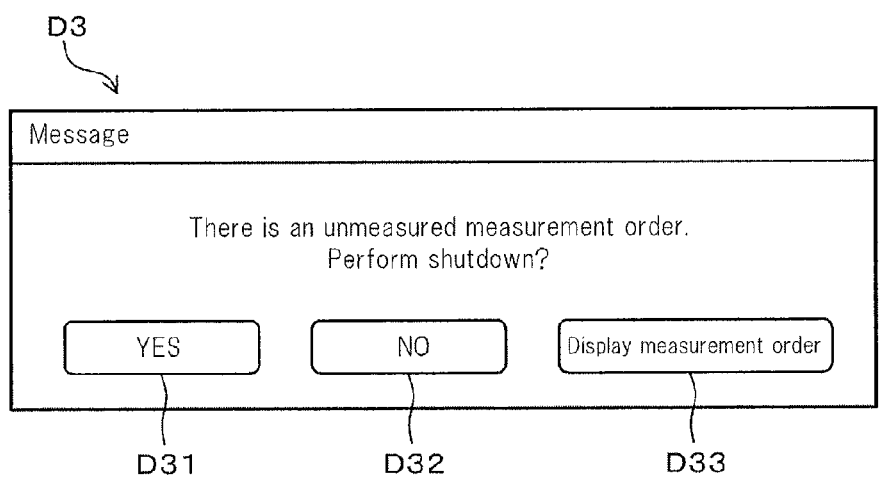
FIG. 11B shows another example of a message dialog.

A summary of the measurement order indicating "unmeasured" is shown in the message dialog D3. The shutdown operation is performed when the button D31 is pressed, and the shutdown operation is not performed when the button D32 is pressed. The message dialog D3 remains open if neither button is pressed; the message dialog D3 is a so-called dialog box, and the shutdown operation is deferred while the dialog box is displayed. Note that the message dialog D3 also may contain a button D33 as shown in FIG. 11B. In this case, when the button D33 is pressed, the measurement record screen D2 of FIG. 9, or a dialog box similar to the measurement record screen D2, is shown on the display section 42.

Referring to FIG. 10, the CPU 401 determines whether the button D31 or the button D32 has been pressed in the message dialog D3 (S122, S124). When the button D31 corresponding to the selection branch [YES] is pressed (S122: YES), the CPU 401 performs the shutdown of the measurement unit that is the destination in S118 (S123). The shutdown is an operation that either turns OFF the power source of the sample analyzer 1 including the measurement unit 31, measurement unit 32, and information processing unit 4 after washing processes have been performed using the washing liquid containers C (power OFF mode), or places a washed measurement unit that has been subjected to the washing process in a standby condition (standby mode). The standby condition is a condition in which the sample analyzer 1 is at standby status and is capable of receiving an instruction to start measurement. The operator may preset execution of either mode as the shutdown operation.

The measurement unit 31 or 32 is subjected to a washing process using the corresponding washing liquid container C according to the take-up operation of FIG. 4B. Thereafter, the power source is turned OFF or the apparatus transitions to the standby condition according to the set mode. When the CPU 401 determines that the button D32 corresponding to the selection branch [NO] has been pressed in the message dialog D3 (S122: NO; S124: YES), the process of S123 is skipped. If none of the buttons is pressed (S124: NO), the determinations of S122 and S124 are repeated and the shutdown deferment continues.

Note that when the standby mode is set and a shutdown process is performed for only one of the two operating measurement units, only one of the measurement units enters the standby condition after the washing process, whereas the remaining measurement unit continues operation. When one measurement unit is in the standby condition and the remaining measurement unit undergoes the shutdown process, both measurement units transition to the standby condition after the washing process has been performed.

When shutdown operation is performed for only one of the two operating measurement units and the power supply OFF mode is set, the washing process is performed and then only the washed measurement unit becomes sleep (that is, a condition in which sample processing is rejected). When a single measurement unit is in the sleep condition and the remaining measurement unit undergoes the shutdown process, the washing process is performed and thereafter the power source of the sample analyzer 1 is turned OFF, including both measurement units and the information processing unit.

The CPU 401 then cancels the washing appointment of the measurement unit (S125), and determines whether a washing appointment is set for the other measurement unit (S126). When a washing appointment is set for the other measurement unit (S126: YES), the process returns to S118, and process of S118 through S125 are performed for the other measurement unit. Alternatively, when washing appointment is not set for the other measurement unit (S126: NO), the transporting unit 2 moves the rack L to the left table 22 (S127).

According to the present embodiment, the operations of S117 through S126 of FIG. 10 are performed when the barcode reader B2a reads the washing liquid ID from the barcode label of the washing liquid container C placed as shown in FIG. 2D (S113: YES of FIG. 10). At this time the CPU 401 of the information processing unit 4 refers to the status information of the measurement order stored in the database 404A. When the status information indicates the sample is "unmeasured" (measurement order), the information processing unit 4 shows the message dialog D3 on the display section 42, and defers the execution of the shutdown operation until an instruction is received from the operator. Hence, automatically starting the shutdown operation can be avoided even when the operator forgets about the presence of an unmeasured sample and starts to transport the washing liquid container C. It is therefore possible to prevent a situation in which an operator becomes aware of the presence of an unmeasured sample after shutdown, but must wait a long time to measure the sample until the shutdown ends or until the sample analyzer 1 is restarted.

According to the present embodiment, the operator can readily comprehend the presence of an unmeasured sample (measurement order) when an unmeasured sample remains by showing the message dialog D3 on the display section 42. Since the message dialog 3 includes the buttons D31 and D32, execution of the shutdown operation can be easily selected by operating the button D31 or D32. When a button D33 is included in the message dialog D3 as shown in FIG. 11B, the operator can verify an unmeasured order by operating the button D33. The operator therefore can suitable determine whether to execute the shutdown operation.

Although the present invention has been described above by way of an embodiment, the present invention is not limited to this embodiment.

For example, although the example of a blood cell counter is used as an example of a measurement unit in the above embodiment, the measurement unit broadly applied insofar as the apparatus is provided with an apparatus for processing a clinical sample. Hence, the measurement unit also may be a urine analyzer, blood coagulation analyzer, immunological analyzer, or biochemical analyzer. Neither is the present invention limited to apparatuses for measuring and analyzing a sample, inasmuch as the invention is also applicable to apparatuses for preparing a smeared sample from a specimen.

The above embodiment is described by way of example in which an input shutdown instruction is dealt with based on having read the barcode of the washing liquid container C. The present invention is not limited to this variation, however.

Suppose, for example, a case in which a shutdown instruction for the measurement unit 31 or measurement unit 32 can be issued from the information processing unit 4. In this case, a button (hereinafter referred to as "shutdown button") for initiating a shutdown is shown on an application screen displayed on the display section 42. When the operator presses this shutdown button, a determination is made as to whether there is an unmeasured order similar to steps S119 through S121 of FIG. 10.

If an unmeasured order does not exist, the information processing unit 4 transmits a shutdown signal to the measurement unit 31 or 32, and the power source is turned OFF for the measurement unit 31 or 32.

If an unmeasured order does exist, the message dialog screen of FIG. 11A or FIG. 11B is displayed. If the [YES] branch is selected, a shutdown signal is transmitted from the information processing unit 4. When the [NO] branch is selected, the operation of the shutdown button is canceled, and the screen returns to the original application screen.

Note that shutdown in this case includes only the operation of turning OFF the power source of the measurement unit and does not include washing using a washing liquid.

Although the shutdown operation in the above embodiment includes washing by aspirating washing liquid from a washing liquid container that holds a special washing liquid and retaining the aspirated washing liquid in the fluid flow circuit, the present invention is not limited to this variation.

The special washing liquid also may be held in a bottle (hereinafter referred to as "washing liquid bottle") installed within the measurement unit. When a shutdown signal is transmitted from the information processing unit 4, the measurement unit 31 inserts a pipette 31d into the bottle, aspirates the washing liquid, and executes washing as in the above embodiment.

A further modification of this embodiment also may connect the bottle to the sample preparing section 312 and the detecting section 313 through a flow path, and move the washing liquid through the flow path.

Although the above embodiment is described by way of example in which a sample analyzer 1 aspirates a sample by a pipette 31d after the sample container T has been moved into the measurement unit by the hand 31a of the measurement unit 31, the present invention is not limited to this variation. Aspiration of the sample also may be performed without moving the sample container T into the measurement unit. Specifically, the sample analyzer 1 may be provided with a pipette at the take-up position P31a to aspirate the sample in the sample container T on the rack transporter 23.

In the above embodiment, when an unmeasured sample (measurement order) exists, the washing liquid container C waits at the take-up position of the corresponding measurement unit until either button D31 or D32 is pressed in the message dialog D3. The present invention is not limited to this variation, however. The washing liquid container C also may wait at another position on the rack transporter 23, for example, the reading position P2. The method of prohibiting shutdown also may be a method in which the washing liquid container C is taken into the measurement unit, but the container transporter 31c (32c) avoids setting the washing liquid container C at the aspirating position P31c (P32c). Another method may be avoiding aspiration of the washing liquid by the pipette 31d (32d).

Although the barcode adhered to the container is read on the rack transporter 23 connecting the right table 21 and the left table 22 in the above embodiment, the present invention is not limited to this variation. For example, the barcode also may be read midway on the transport path of the transporter when the transporter that supplies the rack L to the right table 21 is connected upstream of the transport uniting 2.

Although the above embodiment is described by way of example in which a sample analyzer 1 is provided with two measurement units 31 and 32, a single measurement unit or three or more measurement units also may be provided and, moreover, a smear sample preparing apparatus having a device for aspirating and smearing blood on a slide may be provided in place of a measurement unit.

Note that when the sample analyzer 1 is provided with a smear sample preparing apparatus, a special order is used including the sample ID and whether to prepare a smear sample associated with the sample ID. The status information also includes information indicating whether preparation is completed ("unprepared" or "completed") based on the smear sample preparation order. When preparing to supply a washing liquid container C to either the measurement unit or the smear sample preparation apparatus, the CPU 401 of the information processing unit 4 refers to the status information, and displays the message dialog D3 and whether there is an unmeasured or unprepared sample.

Although the message dialog D3 is displayed insofar as there is an unmeasured sample (measurement order) after referring to the status information in the above embodiment, whether to display the message dialog D3 also may be determined by referring to the recording date/time information of the measurement order.

FIGS. 12A and 12B are flow charts with modified step S120 of the flow chart of FIG. 10. In FIGS. 12A and 12B, only the modified part of the flow chart is shown; the dashed line indicates the modified part from the flow chart of FIG. 10.

Referring to FIG. 12A, the CPU 401 of the information processing unit 4 refers to the status information (S119), then refers to the recording date/time information relating to the day and time the measurement order was recorded (S131). The status information and recording date/time information are stored in the database 404A on the hard disk 404 as mentioned above. The CPU 401 then determines whether there is a measurement order that is unmeasured and the recording date/time is within a predetermined time since the current time (for example, within 24 hours). That is, in the algorithm shown in FIG. 12A, measurement orders that are unmeasured but the recording date/time is not within a predetermined time from the current time are ignored.

When there is an unmeasured measurement order recorded within the predetermined time (S132: YES), the CPU 401 shows the message dialog D3 on the display section 42 similar to the above embodiment (S121). Alternatively, when there is not an unmeasured measurement order recorded within the predetermined time (S132: NO), the process advances to S123.

Referring to FIG. 12B, the CPU 401 of the information processing unit 4 refers to the status information (S119), then refers to the recording date/time information corresponding to the measurement order (S141). The CPU 401 then determines whether there is an unmeasured measurement order with a recording date/time after the date/time the previous washing process was performed (washing date/time) (S142). That is, in the algorithm shown in FIG. 12B, unmeasured measurement orders having a recording date/time before the previous washing process was performed are ignored. Note that the execution date and time of the most recent washing process performed by either the measurement unit 31 or 32 is stored on the hard disk 404.

When there is an unmeasured measurement order recorded after the previous washing process date/time (S142: YES), the CPU 401 shows the message dialog D3 on the display section 42 similar to the above embodiment (S121). Alternatively, when there is not an unmeasured measurement order recorded after the previous washing process date/time (S142: NO), the process advances to S123.

According to the configuration as shown in FIGS. 12A and 12B, even if an unnecessary measurement order, that has been forgotten to be canceled, is remained, the shutdown process is performed without displaying the message dialog D3. Hence, the shutdown process can be performed smoothly.

Note that in S142, the CPU 401 determines whether there is an unmeasured measurement order with a recording date/time that is later than the date/time of the previous shutdown process (shutdown date/time).

In the above embodiment, the status information is referenced to determine whether there is an unmeasured measurement order each time the washing liquid container C is moved to the take-up position of the measurement unit having the washing appointment. Alternatively, the determination whether uncompleted order remains may be skipped when both of two measurement units are working but the washing is done for only one of the two measurement units. In this configuration, if only one of measurement units is working and the washing appointment is set for the working unit, the determination is executed.

Although the existence of an unmeasured measurement order is determined when the washing liquid container C arrives at the take-up position in the above embodiment, the existence of the unmeasured measurement order also may be determined when the barcode is read in S112.

Although the sample container T and the washing liquid container C are placed in the rack L and supplied to the measurement units 31 and 32 in the above embodiment, the sample container T and the washing liquid container C also may be transported one by one placed directly in the rack transporter 23 and supplied to the measurement units 31 and 32 without being set in the rack L.

In the above embodiment, the presence of a container is determined by the barcode unit B2. Classification as a sample container T and washing liquid container C is determined by reading the barcode. The carrier of the identification information is not limited to a barcode. For example, an IC chip representing the sample ID and washing liquid ID may be allocated to a container with an IC reader being used to obtain the identification information, and an RFID (radio frequency identification) representing the sample ID and washing liquid ID may be allocated to a container with the an RFID reader being used to obtain the identification information. When containers having different shapes are established beforehand for the sample and the washing liquid, an optical sensor may be used to distinguish the shape, or the container may be photographed and the shape may be recognized by image analysis. In place of a linear barcode, a two-dimensional code may be used, such as a QR code (registered trademark).

In the above embodiment, when the washing liquid ID is read from the barcode label C1 of the washing liquid container C placed as shown in FIG. 2D, a washing appointment is set according to the position of the washing liquid container C. However, the present invention is not limited to this variation inasmuch as shutdown may be accepted by using a special rack. In this case, when it is determined there is a rack L to be washed by the rack ID read by the barcode reader B2a, the message dialog D3 may be displayed if there is an unmeasured measurement order.

Although whether a measurement of a sample has been completed is determined using the status information in the above embodiment, the status information need not be used. When measurement of a sample ends based on the measurement order, the measurement order can be erased from the database 404A instead of S116 of FIG. 10. In this case, measurement orders stored on the hard disk 404 all are unmeasured. Therefore, in this case, the determination of existence of unmeasured measurement order can be simply done based on whether any order remains in the database 404A or not.

Although the measurement units 31 and 32 enter a power OFF condition, inactive condition, or standby condition after washing has been executed in the above embodiment, the present invention is not limited to this variation inasmuch as the measurement units 31 and 32 may be restarted, or the operator may set the power OFF condition, inactive condition, standby condition, or restart the units by an application of the information processing unit 4.

When the power OFF mode is set in the above embodiment, shutdown process is performed for the corresponding measurement unit according to the deployment rule shown in FIG. 2D. However, the invention is not limited to this variation; when the power OFF mode is set, the shutdown process may be executed only when a washing liquid container C is set at both holding positions 1 and 2 as shown in the condition of FIG. 2D. In the shutdown process in this instance, after the washing process is performed in parallel in both measurement units using the washing liquid containers C held at the holding positions 1 and 2, the power is turned OFF to the sample analyzer 1 including both measurement units and the information processing unit 4. When a rack L which holds a washing liquid container C only at one holding position, either holding position 1 or 2, and the rack L is placed on the right table 21, a shutdown instruction by the rack L is invalid and the rack L is moved as is to the left table 22. Note that when the operation in the power OFF mode is modified in this way, the power is turned OFF to both measurement units with approximately the same timing without the inactive condition mentioned above.

When there is an unmeasured sample in the above embodiment (S120: YES in FIG. 10), the message dialog D3 is displayed and the operator presses either the button D31 or D32 to select whether to perform the shutdown process. However, the present invention is not limited to this variation; when an unmeasured sample is present, the normal shutdown process may be prohibited without displaying the message dialog D3. Displaying the message dialog D3 as in the above embodiment, and not performing the normal shutdown process also may be set by the operator.

Although the message dialog D3 is displayed when there is an unmeasured sample in the above embodiment (S120: YES in FIG. 10), the invention is not limited to this variation inasmuch as an audio sound may be emitted from a speaker provided in the information processing unit 4 to warn that an unmeasured sample is present and to allow the transport of the washing liquid container C to be suspended. When a shutdown instruction is issued and the operator is at a position some distance from the apparatus, the operator is soon alerted that the execution of the shutdown is deferred by the emitted audio even when the operator is separated from the apparatus after issuing an instruction to start the transport of the washing liquid container C.

Although the shutdown prohibition is released by pressing the button D31 displayed on the screen when the shutdown operation has been deferred in the above embodiment, the prohibition also may be released by other means. For example, the prohibition may be released by pressing a hardware button installed on the body of the measurement unit, or the prohibition may be released by a predetermined key operation.

When there is an unmeasured sample in the above embodiment (S120: YES in FIG. 10), a message dialog D3 is displayed and includes a button D32 to stop the shutdown operation. However, a message may also be displayed on the message dialog D3 urging the operator to perform a predetermined operation (for example, pressing a predetermined key) via the input section 41.

In the above embodiment, when the message dialog D3 shown in FIG. 11B is displayed and the button D33 is pressed, the measurement record screen D2 of FIG. 9 or a dialog similar to the measurement record screen D2 is displayed. However, the present invention is not limited to this variation; after the message dialog D3 has been displayed, the measurement record screen D2 or a dialog similar to the measurement record screen D2 may be displayed automatically with a predetermined timing (for example, after 10 seconds has elapsed). In this case, a list including only the unmeasured measurement order may be displayed instead of the measurement record screen D2.

In the above embodiment, the measurement order, status information, and recording date/time are stored in the database 404A on the hard disk 404 of the information processing unit 4. However, the present invention is not limited to this variation and when a host computer 5 is connected to the information processing unit 4 so as to allow communication therebetween, the measurement order, status information, and recording date/time may be stored on the hard disk 52 of the host computer 5 as shown in FIG. 13.

In this case, the host computer 5 can display the order input screen D1 similar to the information processing unit 4, and is configured to accept a measurement order record from the operator through the screen.

An example of a series flow is given using the host computer 5. The physician who examined the patient receives the result of the examination, and determines the items that need to be measured for the patient. The physician enters the determined measurement items as a measurement order in the host computer 5. The host computer 5 associates and stores the measurement order, status information, and recording date/time information with the sample ID on the hard disk 52. The physician issues a barcode indicating the sample ID, and adheres the barcode to the sample container holding the collected sample.

The barcode adhered to the sample container is read when the sample container holding the sample collected from the patient arrives at the sample analyzer 1. In S114 of FIG. 10, the information processing unit 4 transmits to the host computer 5 the information with an additional summary of an order query of the sample ID represented by the read barcode as shown in FIG. 13B. The host computer 5 reads the measurement order stored on the hard disk 52, and transmits the information to the information processing unit 4. The measurement units 31 and 32 of the information processing unit 4 perform measurements on the sample based on the received measurement order. When the measurement are completed, the information processing unit 4 transmits to the host computer 5 the information with added information of the completion for the sample ID as shown in FIG. 13C. The host computer 5 updates the content of the status information associated with the sample ID to "completed."

In S119 of FIG. 10, the information processing unit 4 transmits to the host computer 5 the information with added request for status information of the washing liquid ID as shown in FIG. 13D. The host computer 5 refers to the status information stored on the hard disk 52, and transmits whether there is an unmeasured measurement order to the information processing unit 4, and the information processing unit 4 performs the determination of S120 based on the received information. Note that the host computer 5 also may transmit to the information processing unit 4 the measurement order with the latest recording date/time, and the number of unmeasured measurement orders together with the unmeasured measurement orders, or in replacement thereof.

Thus, when the measurement order is stored on the hard disk 52 of the host computer 5, the button D33 of the message dialog D3 shown in FIG. 11B is used to display the content transmitted from the host computer 5 to the information processing unit 4 according to the query on the existence of unmeasured measurement orders.

The above embodiment shows by way of example a shutdown instruction by reading the washing liquid ID. Specifically, when the washing liquid ID was read from the barcode label C1 of the washing liquid container C (S113: YES in FIG. 10), the operation shown in S117 through S126 of FIG. 10 was performed as a shutdown operation. However, the present invention is not limited to this variation inasmuch as the processes of S117 through S126 also may be performed when a shutdown instruction and washing instruction are manually entered by the operator.

When the operator manually enters the shutdown instruction or washing instruction, the sample analyzer need not have a transporting unit.

Figure 14:
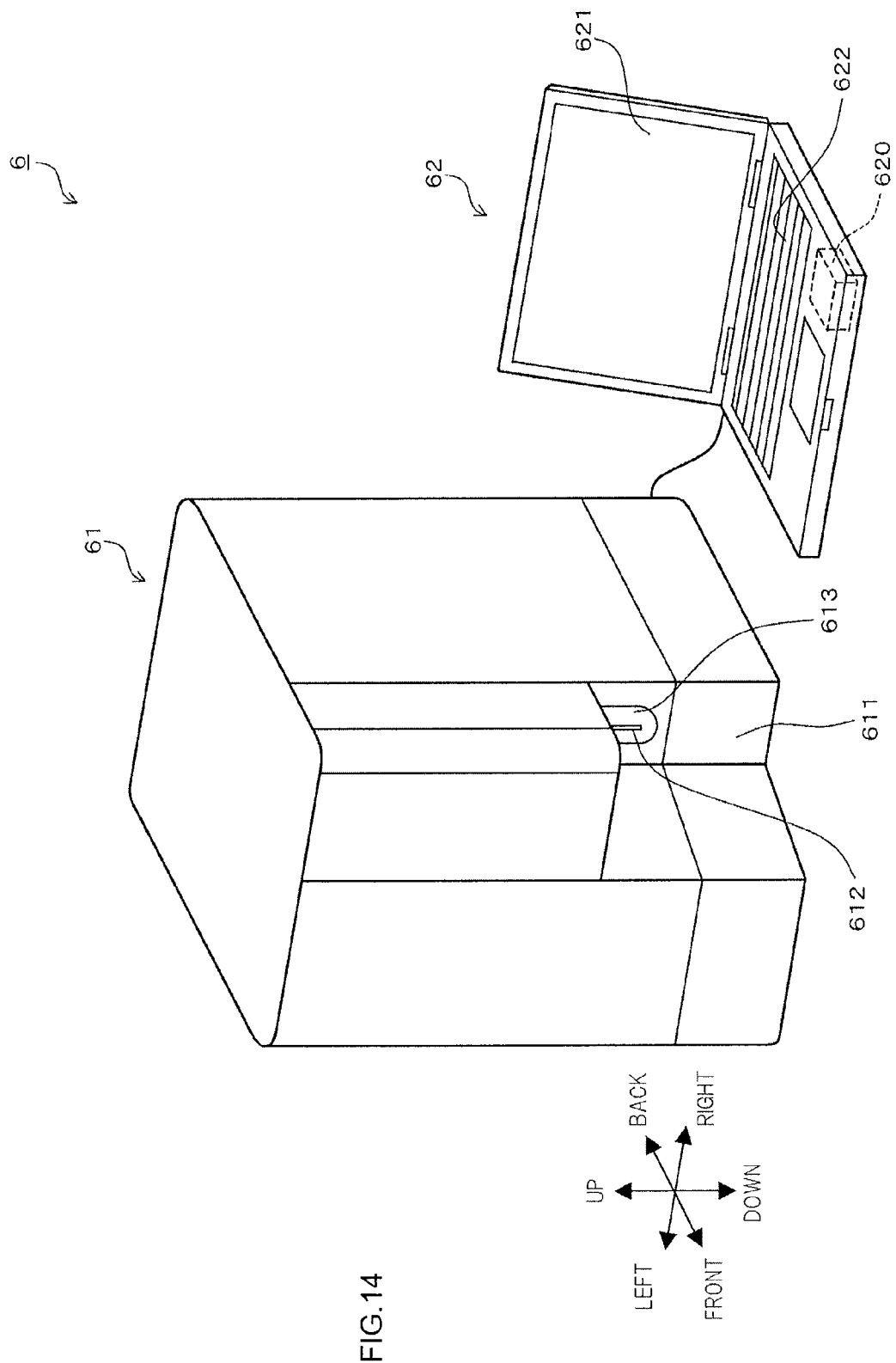
FIG. 14 is an external perspective view of another example of a sample analyzer.

FIG. 14 is an exterior perspective view of an example of a sample analyzer 6 that is not provided with a transporting unit. The sample analyzer 6 is configured by a measurement unit 61, and an information processing unit identical to the information processing unit 4.

A concavity 611 is formed on the bottom right part on the front of the measurement unit 611. A pipette 612 is installed so as to protrude on the top surface of the concavity 611, and a start switch 613 is provided on the back side of the concavity 611. The operator presses the start switch 613 when the pipette 612 is inserted in the container to issue an instruction to aspirate the liquid within the container. The measurement unit 61 has a handheld barcode reader 614. The operator reads the barcodes of the containers one by one using the barcode reader 614. Either the sample ID assigned specifically to the sample or the washing liquid ID representing the washing liquid is stored on the barcode. In other aspects the structure of the measurement unit 61 is similar to the measurement units 31 and 32.

The information processing unit 62 has a CPU 620, display section 621, and input section 622, and is connected to the measurement unit 61 so as to allow communication therebetween. The information processing unit 62 has a hard disk (not shown in the drawing), and a database of associated measurement orders, status information, and recording information is stored on the hard disk similar to the information processing unit 4. In other aspects the structure of the information processing unit 62 is similar to the information processing units 31 and 32.

When measuring a sample, the operator reads the barcode adhered to the sample container via the barcode reader 614. After the barcode has been read, the pipette is inserted in the sample container, and the start switch 613 is pressed.

When executing the washing process and shutdown process, the barcode adhered to the washing liquid container is read by the barcode reader 614. After the barcode has been read, the pipette is inserted in the washing liquid container, and the start switch 613 is pressed.

Figure 15:
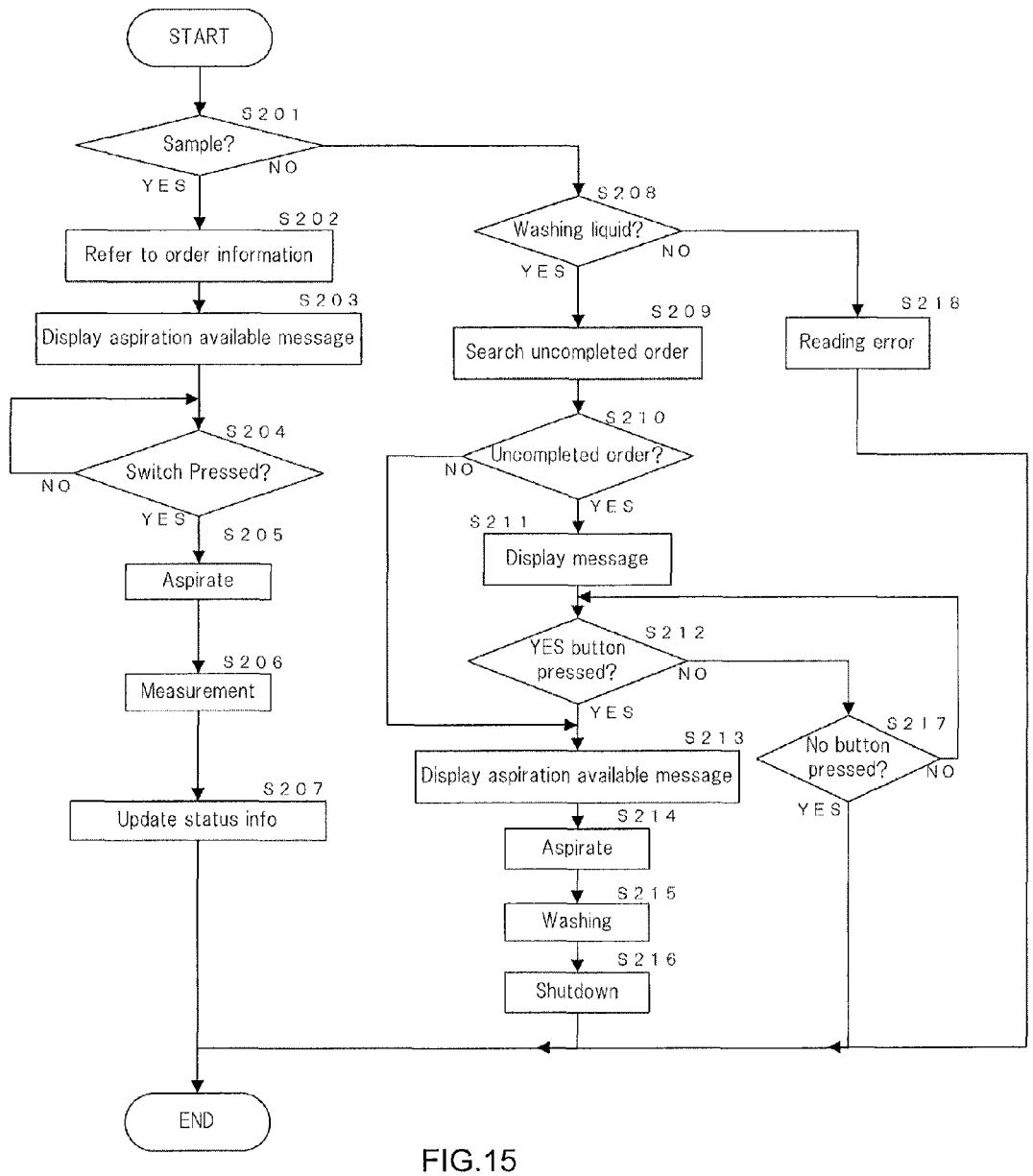
FIG. 15 is a flow chart showing the control operation of an information processing unit of a modification.

FIG. 15 is a flow chart showing the processing performed by the information processing unit 62.

A series of processes start when the ID is input by the operator reading the barcode of the container via the barcode reader 614. The CPU 620 of the information processing unit 62 determines whether the input ID is a sample ID.

When the input ID is a sample ID (S201: YES), the CPU 620 refers to the measurement order using the input sample ID as a key (S202). When the measurement order associated with the sample ID is retrieved, the CPU 620 shows a message indicating the sample can be aspirated on the display section 621 (S203). The start switch 613 is invalid until the message is displayed, and aspiration will not start if the switch is pressed before the message is displayed. The CPU 620 validates the start switch 613 together with the message display. The CPU 620 determines whether the start switch 613 has been pressed (S204). When the start switch 613 has been pressed, the CPU 620 performs aspiration in the measurement unit 61 (S205), and performs the measurements (S206). The status information of the measurement order corresponding to the sample ID is then updated to "completed" (S207), and the process ends.

When the input ID is not a sample ID (S201: NO), the CPU 620 determines whether the ID is a washing liquid ID (S208). When the ID is not a washing liquid ID (S208: NO), the CPU 620 shows an error message on the display section 621 as a barcode reading error (S218).

When the input ID is a washing liquid ID (S208: YES), the CPU 620 refers to the hard disk and verifies the existence of an uncompleted measurement order (S209). If an uncompleted order exists (S210), the CPU 620 shows the message dialog of FIG. 11A or 11B on the display section 621 (S211). When [YES] is selected on the screen (S212: YES), the CPU 620 shows a message indicating the washing liquid can be aspirated on the display section 621 (S213). At the same time the CPU 620 validates the start switch 613. In the subsequent steps S214 through S216, aspiration of the washing liquid, washing process, and shutdown process are performed. When [YES] is not selected in step S212, a determination is made whether [NO] is selected (S217); if no selection branch is chosen the process returns to step S212 and the process loops until any selection branch is chosen. When [NO] is selected in step S217 (S217: YES), the input ID is erased and the process ends.

When there is no uncompleted order in step S210 (S210: NO), the CPU 620 skips steps S211 and S212, and moves to displaying the message indicating aspiration is possible.

Note that the present invention is not limited to the above described embodiments and may be variously modified insofar as such modification are within the scope of the claims.

What is claimed is:

1. A sample processing apparatus comprising:
    a sample processing section configured to perform a process on a sample; and
    a controller configured to execute an order defining a process to be performed on a sample and to cause the sample processing section to perform the process on the sample according to the order,
    wherein when the controller receives an instruction to perform a shutdown operation, the controller is programmed to perform the following operations comprising:
        prohibiting the execution of the shutdown operation if an unexecuted order remains; and
        causing the sample processing section to perform the shutdown operation if there is no unexecuted order,
    further wherein the sample processing apparatus further comprises a communication interface for communicating with a host computer for managing orders, and the controller is programmed to obtain an order from the host computer with the communication interlace, and
    further wherein the controller is programmed to query the host computer as to whether an unexecuted order exists via the communication interface when the shutdown instruction is received.

2. The sample processing apparatus of claim 1, wherein
    the sample processing section is configured to aspirate a sample, flow the aspirated sample in a fluid circuit, and perform a measurement on the sample; and
    the shutdown operation comprises operations of washing the fluid circuit by aspirating a washing liquid, and flowing the aspirated washing liquid through the fluid circuit, and turning OFF the power source after washing is completed.

3. The sample processing apparatus of claim 2, wherein the shutdown operation comprises an operation of retaining washing liquid in the fluid circuit for a predetermined time.

4. The sample processing apparatus of claim 2, wherein the washing liquid is a chlorine-based cleaning solution.

5. The sample processing apparatus of claim 1, further comprising an output section, wherein the controller causes the output section to output an notice indicating the existence of an unexecuted order when prohibiting the execution of the shutdown operation.

6. The sample processing apparatus of claim 1, further comprising a display section, wherein when prohibiting the execution of the shutdown operation, the controller is programmed to show, on the display section, a screen for receiving an instruction from an operator concerning whether to continue the shutdown operation;
    if an instruction to continue the shutdown operation is received, the controller is programmed to withdraw the prohibition and performs the shutdown operation; and
    if an instruction to not continue is received, the controller is programmed to cancel the shutdown operation.

7. The sample processing apparatus of claim 1, further comprising a database for storing the orders,
    wherein the controller is programmed to control the sample processing section according to an order stored in the database, and
    the controller is programmed to prohibit an execution of the shutdown operation if an unexecuted order remains in the database when the shutdown instruction is received.

8. The sample processing apparatus of claim 7, wherein when a process of a sample is completed by the sample processing section, the controller updates a status of an order corresponding to the sample stored in the database to executed status.

9. The sample processing apparatus of claim 2, wherein
    the sample processing section comprises a pipette configured to aspirate a sample from a sample container at a aspirating position, and a fluid circuit configured for processing the aspirated sample; and
    the shutdown operation comprises an operation for aspirating washing liquid with the pipette from a washing liquid container that accommodates the washing liquid, and retaining the washing liquid in the fluid circuit.

10. The sample processing apparatus of claim 1, further comprising:
    a transporting section configured to transport a container accommodating a washing liquid to an aspirating position;
    wherein when the shutdown operation is prohibited, the controller is programmed to suspend the transport of the washing liquid container by the transporting section before the washing liquid container arrives at the aspirating position.

11. The sample processing apparatus of claim 9, further comprising a reading section configured to read identification information affixed to a container, wherein
    when the read identification information is identification information of a washing liquid container, the controller is programmed to use the identification information as the shutdown instruction, and
    when the read identification information is identification information of a sample container, the controller is programmed to use the identification information to retrieve an order.

12. The sample processing apparatus of claim 6, wherein the screen further comprises a button, and the controller is programmed to show on the display section a list of one or more unexecuted orders when the button is operated.

13. The sample processing apparatus of claim 1, wherein if an order remains unexecuted but the order is already invalid, the controller is programmed to ignore the order in the determination of whether to perform a shutdown operation.

14. The sample processing apparatus of claim 1, wherein the order comprises a designation of one or more measurement items to be measured selected from a plurality of measurement items.

15. A sample processing apparatus comprising:
a sample processing section configured to perform a process on a sample; and
a controller configured to execute an order defining a process to be performed on a sample and to cause the sample processing section to perform the process on the sample according to the order,
wherein when the controller receives an instruction to perform a shutdown operation, the controller is programmed to perform the following operations comprising:
prohibiting the execution of the shutdown operation if an unexecuted order remains; and
causing the sample processing section to perform the shutdown operation if there is no unexecuted order,
further wherein the sample processing section is configured to aspirate a sample, flow the aspirated sample in a fluid circuit, and perform a measurement on the sample, and the shutdown operation comprises operations of washing the fluid circuit by aspirating a washing liquid, and flowing the aspirated washing liquid through the fluid circuit, and turning OFF the power source after washing is completed,
further wherein the sample processing section comprises a pipette configured to aspirate a sample from a sample container at a aspirating position, and a fluid circuit configured for processing the aspirated sample, and the shutdown operation comprises an operation for aspirating washing liquid with the pipette from a washing liquid container that accommodates the washing liquid, and retaining the washing liquid in the fluid circuit, and
further wherein the sample processing apparatus further comprises a reading section configured to read identification information affixed to a container, wherein
when the read identification information is identification information of a washing liquid container, the controller is programmed to use the identification information as the shutdown instruction, and
when the read identification information is identification information of a sample container, the controller is programmed to use the identification information to retrieve an order.

16. The sample processing apparatus of claim 15, wherein the shutdown operation comprises an operation of retaining washing liquid in the fluid circuit for a predetermined time.

17. The sample processing apparatus of claim 15, wherein the washing liquid is a chlorine-based cleaning solution.

18. The sample processing apparatus of claim 15, further comprising an output section, wherein the controller causes the output section to output an notice indicating the existence of an unexecuted order when prohibiting the execution of the shutdown operation.

19. The sample processing apparatus of claim 15, further comprising a display section,
wherein when prohibiting the execution of the shutdown operation, the controller is programmed to show, on the display section, a screen for receiving an instruction from an operator concerning whether to continue the shutdown operation;
if an instruction to continue the shutdown operation is received, the controller is programmed to withdraw the prohibition and performs the shutdown operation; and
if an instruction to not continue is received, the controller is programmed to cancel the shutdown operation.

20. The sample processing apparatus of claim 15, further comprising a database for storing the orders;
wherein the controller is programmed to control the sample processing section according to an order stored in the database; and
the controller is programmed to prohibit an execution of the shutdown operation if an unexecuted order remains in the database when the shutdown instruction is received.

21. The sample processing apparatus of claim 20, wherein when a process of a sample is completed by the sample processing section, the controller updates a status of an order corresponding to the sample stored in the database to executed status.

22. The sample processing apparatus of claim 15, wherein a communication interface for communicating with a host computer for managing orders, and the controller is programmed to obtain an order from the host computer with the communication interface.

23. The sample processing apparatus of claim 22, further comprising a transporting section configured to transport a container accommodating a washing liquid to an aspirating position,
wherein when the shutdown operation is prohibited, the controller is programmed to suspend the transport of the washing liquid container by the transporting section before the washing liquid container arrives at the aspirating position.

24. The sample processing apparatus of claim 15, wherein the screen further comprises a button, and the controller is programmed to show on the display section a list of one or more unexecuted orders when the button is operated.

25. The sample processing apparatus of claim 15, wherein if an order remains unexecuted but the order is already invalid, the controller is programmed to ignore the order in the determination of whether to perform a shutdown operation.

26. The sample processing apparatus of claim 15, wherein the order comprises a designation of one or more measurement items to be measured selected from a plurality of measurement items.

27. A sample processing apparatus comprising:
a sample processing section configured to perform a process on a sample; and
a controller configured to execute an order defining a process to be performed on a sample and to cause the sample processing section to perform the process on the sample according to the order,
wherein when the controller receives an instruction to perform a shutdown operation, the controller is programmed to perform the following operations comprising:
prohibiting the execution of the shutdown operation if an unexecuted order remains; and
causing the sample processing section to perform the shutdown operation if there is no unexecuted order,
further wherein the sample processing apparatus further comprises a display section, wherein when prohibiting the execution of the shutdown operation, the controller is programmed to show, on the display section, a screen for receiving an instruction from an operator concerning whether to continue the shutdown operation;

if an instruction to continue the shutdown operation is received, the controller is programmed to withdraw the prohibition and performs the shutdown operation; and if an instruction to not continue is received, the controller is programmed to cancel the shutdown operation, and further wherein the screen further comprises a button, and the controller is programmed to show on the display section a list of one or more unexecuted orders when the button is operated.

* * * * *

UNITED STATES PATENT AND TRADEMARK OFFICE
CERTIFICATE OF CORRECTION

| | |
|---|---|
| PATENT NO. | : 9,164,110 B2 |
| APPLICATION NO. | : 13/722041 |
| DATED | : October 20, 2015 |
| INVENTOR(S) | : Daigo Fukuma et al. |

It is certified that error appears in the above-identified patent and that said Letters Patent is hereby corrected as shown below:

In the Claims

In column 21, claim 1, line 42, after "with the communication" replace "interlace," with --interface,--.

Signed and Sealed this
Twenty-ninth Day of March, 2016

Michelle K. Lee
*Director of the United States Patent and Trademark Office*